US012083205B2

(12) United States Patent
Faunce et al.

(10) Patent No.: US 12,083,205 B2
(45) Date of Patent: Sep. 10, 2024

(54) ESTERQUAT COMPOSITIONS

(71) Applicant: Stepan Company, Northfield, IL (US)

(72) Inventors: James A. Faunce, North Aurora, IL (US); Renata A. Butikas, Chicago, IL (US); Randal J. Bernhardt, Spring Grove, IL (US); Sarah E. Kovach, Palatine, IL (US); Teresa Germain, Orland Park, IL (US); Patrick Shane Wolfe, Palatine, IL (US); Leonard Frank Zaporowski, Arlington Heights, IL (US); Anatoliy A. Dameshek, Indian Creek, IL (US)

(73) Assignee: Stepan Corporation, Northfield, IL (US)

( * ) Notice: Subject to any disclaimer, the term of this patent is extended or adjusted under 35 U.S.C. 154(b) by 798 days.

(21) Appl. No.: 17/145,999

(22) Filed: Jan. 11, 2021

(65) Prior Publication Data
US 2021/0128432 A1    May 6, 2021

Related U.S. Application Data

(63) Continuation of application No. PCT/US2019/041684, filed on Jul. 12, 2019.

(51) Int. Cl.
*A61K 8/41*     (2006.01)
*A61K 8/37*     (2006.01)
*A61K 8/9789*   (2017.01)
*A61Q 5/02*     (2006.01)

(52) U.S. Cl.
CPC ............... *A61K 8/416* (2013.01); *A61K 8/37* (2013.01); *A61K 8/9789* (2017.08); *A61Q 5/02* (2013.01); *A61K 2800/596* (2013.01)

(58) Field of Classification Search
CPC ..... A61K 8/416; A61K 8/37; A61K 2800/596
See application file for complete search history.

(56) References Cited

U.S. PATENT DOCUMENTS

| 4,886,660 | A | 12/1989 | Patel et al. |
| 4,891,214 | A | 1/1990 | Stevens et al. |
| 5,869,716 | A | 2/1999 | Subirana et al. |
| 5,886,201 | A | 3/1999 | Bonastre et al. |
| 5,916,863 | A | 6/1999 | Lacobucci et al. |
| 6,376,455 | B1 | 4/2002 | Friedli et al. |
| 6,641,803 | B1 | 11/2003 | Kahre et al. |
| 2001/0036909 | A1* | 11/2001 | Levinson ............ C11D 17/047 510/330 |
| 2002/0002298 | A1 | 1/2002 | Bigorra Llosas et al. |
| 2003/0026774 | A1 | 2/2003 | Milbradt et al. |
| 2010/0216679 | A1* | 8/2010 | Batchelor ............ C11D 3/2093 510/107 |
| 2016/0023989 | A1 | 1/2016 | Allen et al. |

FOREIGN PATENT DOCUMENTS

| DE | 19805703 | 8/1999 |
| DE | 10237031 | 2/2004 |
| EP | 0367939 | 5/1990 |
| EP | 0580527 | 1/1994 |
| EP | 890357 A2 * | 1/1999 | ............. A61K 47/08 |
| EP | 1149891 | 10/2001 |
| JP | 2005206573 | 8/2005 |
| WO | 9725398 | 7/1997 |
| WO | 9935223 | 7/1999 |
| WO | 0027355 | 5/2000 |
| WO | 200028950 | 5/2000 |
| WO | 2003060046 | 7/2003 |
| WO | 2006027214 | 3/2006 |
| WO | 2012076177 | 6/2012 |
| WO | 2020000172 | 1/2020 |

OTHER PUBLICATIONS

Subila, S. "Determination of Saponification and Iodine Value of Sunflower Oil" Int. J. Inn. Res. Adv. Stud. 2016, 3(13), pp. 123-125 (Year: 2016).*
Machine translation of Bigorra et al. (EP 0890357), Feb. 6, 1998, pp. 1-15 (Year: 1998).*
International Searching Authority, International Search Report and Written Opinion, Application No. PCT/US19/41684, mailed Nov. 13, 2019, 18 pages.
Europe Patent Office, Extended Search Report, Application No. 19835193.4, mailed Jun. 15, 2022, 13 pages.
Intellectual Property Office of Singpore, Search Report and Written Opinion, Application No. 11202013227U, mailed May 11, 2022, 13 pages.
European Patent Office, Communication pursuant to Rule 114(2) EPC, application No. 19835193.4, mailed Oct. 18, 2021, 3 pages.
International Search Report, Application No. PCT/EP2011/006186, mailed Oct. 29, 2013, 5 pages.
Indonesia Patent Office, Office Action, P00202100200, mailed Nov. 4, 2022, 2 pages.

* cited by examiner

*Primary Examiner* — Andrew S Rosenthal
(74) *Attorney, Agent, or Firm* — McAndrews, Held & Malloy, Ltd.

(57) ABSTRACT

Esterquat compositions are disclosed that comprise, based on the weight of the composition, 0% to about 70% by weight of a solvent, and about 30% to 100% by weight of a mixture comprising about 50% to about 80% by weight, based on the weight of the mixture, of esterquats and about 20% to about 50% by weight, based on the weight of the mixture, of mono- and diglycerides. The esterquat compositions can be prepared by the direct esterification of a natural oil with an alkanolamine, followed by quaternization in the presence of the solvent. The esterquat compositions can be formulated into hair care compositions that provide improved wet and dry combing properties.

18 Claims, 14 Drawing Sheets

Figure 3. The "Quat" referred to in this figure is 85% Sunflower Oil/MDEA/MeCl Quat in 15% PG.

Figure 5. DREWMULSE® GMO is an unsaturated oleic-acid based monoglyceride/diglyceride.

Figure 6. GMO refers to DREWMULSE® GMO.

Figure 8. LUMULSE® GML is a saturated lauric-acid based monoglyceride/diglyceride.

Figure 11. Reference line refers to performance of the Sunflower Oil/MDEA/MeCl Quat.

ESTERQUAT COMPOSITIONS

CROSS-REFERENCE TO RELATED APPLICATIONS

This application is a continuation of and claims priority to PCT Application No. US2019/041684, filed Jul. 12, 2019, which claims priority to U.S. Provisional Application No. 62/839,081, filed Apr. 26, 2019, and U.S. Provisional Application No. 62/697,235, filed Jul. 12, 2018. The entire specifications of the PCT and provisional applications referred to above are hereby incorporated by reference.

FIELD OF THE INVENTION

The present technology relates to esterquat compositions that are useful in compositions, such as hair care compositions. In particular, the present technology relates to esterquat compositions that comprise a synergistic mixture of at least one esterquat and mono- and di-glycerides that provides better wet and dry combing than either the esterquat or mono- and di-glycerides alone. The present technology also relates to hair care compositions comprising the esterquat composition, and a process for making the esterquat composition.

BACKGROUND OF THE INVENTION

Quaternary ammonium compounds have been used as hair conditioning agents for a number of years. Two of the most common hair conditioner agents are behentrimonium chloride (BTAC) and cetrimonium chloride (CETAC). Although both actives work well as conditioning agents, they have certain drawbacks. BTAC and CETAC have unfavorable environmental profiles and their use in conditioning compositions has been under scrutiny. Since 2014, the European Union has restricted these agents in both leave-on and rinse-off products. As raw materials, both BTAC and CETAC are irritating and/or toxic if in contact with skin, and are very toxic to aquatic life, with long-lasting effects. Another drawback is that liquid forms of BTAC and CETAC are typically only available at fairly low active concentrations of 25-30% active. Products with higher concentrations of actives are available, but require dilution with flammable solvents, such as isopropyl alcohol (IPA), to maintain fluidity, or are in the form of pastilles or solids that require heating/melting.

Manufacturers have sought other quaternary ammonium compounds that can deliver conditioning performance without the drawbacks of BTAC and CETAC. Esterquat quaternary ammonium compounds (esterquats) have been used as a hair conditioning active. Such esterquats are typically made from fatty acids reacted with an amine, such as triethanolamine (TEA) or methyl diethanolamine (MDEA) and then quaternized. Use of fatty acids allows better control over the fatty acid chains reacting with the alkanolamine to make the esteramine, whose amine portion is then quaternized, and provides a "pure" molecule compared with oils containing fatty acids in triglyceride form. Although esterquats are less toxic than BTAC and CETAC from an environmental standpoint, they do not perform as well as BTAC and CETAC as a hair conditioning agent. Esterquats are also usually in a solid or paste form, and require heating/melting or dilution with a solvent, such as IPA or ethanol, which could release volatile organic compounds (VOCs) into the environment.

There is a need in the art for esterquat compositions that can deliver hair care performance that is better than CETAC and at least equal to BTAC, but also has a better environmental profile than BTAC and CETAC. There is also a need for an esterquat composition that is in a liquid form at higher active levels, such as 50% active or more.

SUMMARY OF THE INVENTION

In one aspect, the present technology is directed to a composition comprising:
(a) about 30% to about 100% by weight, based on the weight of the composition, of a mixture of one or more esterquats and one or more glycerides, wherein the esterquats comprise about 50% to about 80%, preferably about 55% to about 75% by weight of the mixture, and the glycerides comprise about 20% to about 50%, preferably about 250% to about 45% by weight of the mixture; and
(b) 0% to about 70% by weight, based on the weight of the composition, of a solvent suitable for personal care.

In some embodiments, the composition comprises about 30% to about 95%, alternatively about 30% to about 90% by weight of the mixture of one or more esterquats and one or more glycerides, and about 5% to about 70%, alternatively about 10% to about 70% by weight of solvent.

In another aspect, the present technology is directed to a composition that comprises 0.01% to about 30% by weight, based on the weight of the composition, of a composition active comprising one or more esterquats in an amount of about 50% to about 80%, preferably about 55% to about 75% by weight, based on the weight of the composition active, and one or more glycerides in an amount of about 20% to about 50%, preferably about 25% to about 45% by weight based on the weight of the composition active; optionally, one or more additional components; and diluent to balance the composition to 100%. In one embodiment, the composition is a hair conditioning composition.

In a further aspect, the present technology is directed to a process for preparing a liquid esterquat composition wherein the process comprises (a) reacting a natural oil with an alkanolamine to obtain an intermediate mixture comprising monoesteramines, diesteramines, monoglycerides, diglycerides, glycerin, and free amines; (b) combining the intermediate mixture with an alkylating agent and, optionally, a solvent to form a reaction mixture; and (c) quaternizing the esteramines in the intermediate mixture with the alkylating agent to form esterquats, wherein the resulting composition comprises (i) about 30% to about 100% by weight, based on the weight of the composition, of a mixture of about 50% to about 80% by weight esterquats and about 20% to about 50% by weight glycerides, based on the weight of the mixture, and (ii) solvent in an amount of 0% to about 70% by weight based on the weight of the composition.

In some embodiments, the intermediate mixture comprises a solvent, and the esteramines are quaternized in the presence of the solvent to form a resulting composition which comprises about 30% to about 95%, alternatively about 30% to about 90% by weight, based on the weight of the composition, of a mixture of about 50% to about 80% by weight esterquats and about 20% to about 50% by weight glycerides, and solvent in an amount of about 5% to about 70%, alternatively about 10% to about 70% by weight, based on the weight of the composition.

In another aspect, the present technology is directed to a hair care composition that comprises 0.01% to about 30% by weight, based on the weight of the composition, of a composition active, wherein the composition active comprises (i) at least one esterquat derived from a fatty acid source having C8-C32 carbon chains, and (ii) optionally, a glyceride component derived from a fatty acid source having C8-C32 carbon chains, wherein the glyceride component comprises at least one monoglyceride, or diglyceride, or a combination thereof, wherein at least 60% of the carbon chains in the composition active have at least one carbon-carbon double bond. In some embodiments, at least 50% of the carbon chains having carbon-carbon double bonds have at least two carbon-carbon double bonds.

DETAILED DESCRIPTION OF THE PREFERRED EMBODIMENTS

Figure 1:
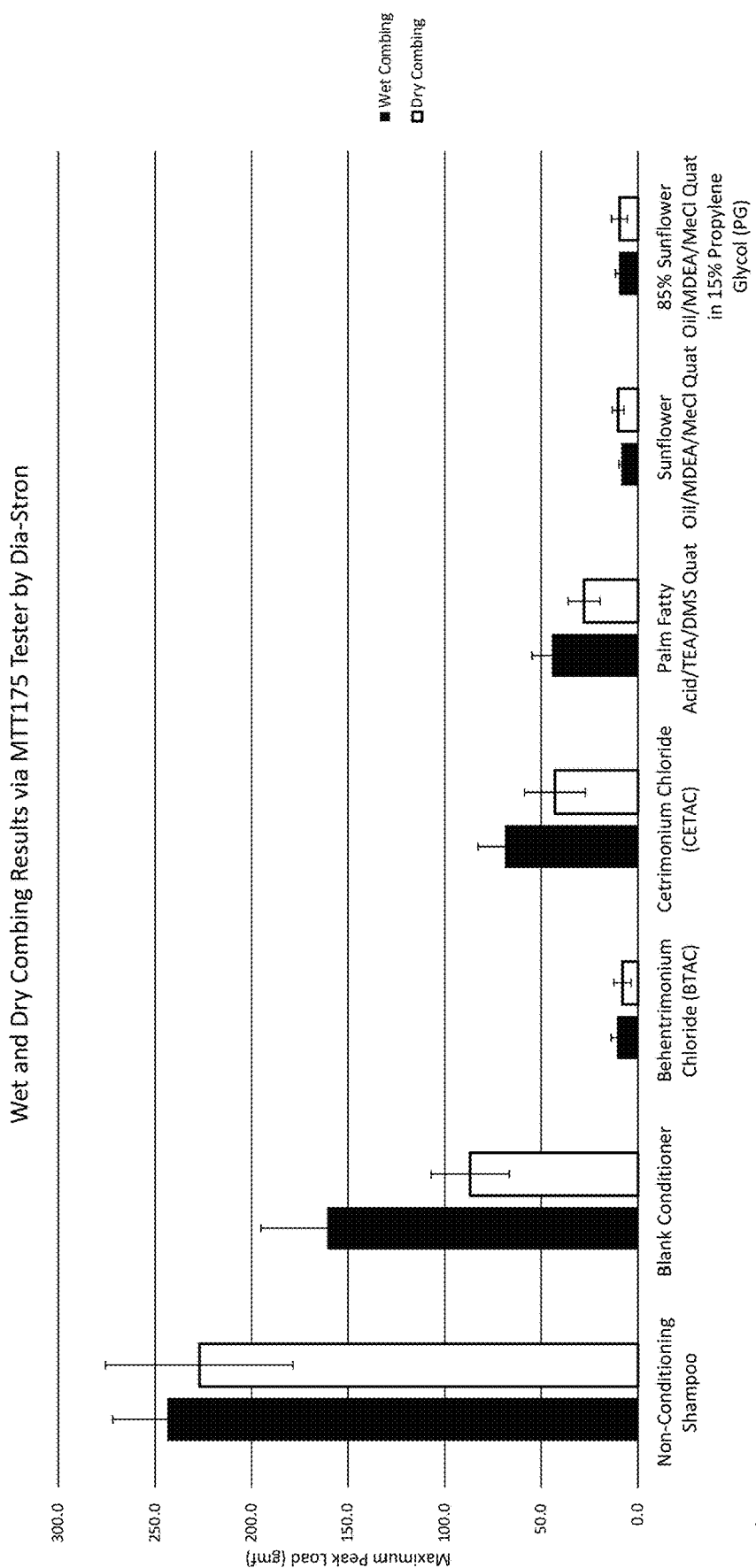
FIG. 1 is a graph comparing the wet and dry combing results of hair conditioning compositions prepared with esterquat compositions of the present technology vs. compositions prepared with conventional quaternary ammonium compounds.

The compositions of the present technology comprise particular esterquats and mono- and diglycerides that together provide an effective hair conditioning agent that is biodegradable, and provides conditioning performance that is better than CETAC and comparable to BTAC. In some embodiments, the compositions also comprise from 1%-70%, alternatively about 5% to about 70%, alternatively about 10% to about 70% by weight of a suitable solvent capable of diluting 30%-99% by weight of the combined esterquat and glyceride to form a low viscosity liquid product.

In general, the esterquats of the present technology are prepared by combining a natural oil or other fatty acid source and an alkanolamine, typically at a starting temperature at which the natural oil or fatty acid source is a liquid or molten, optionally adding a catalyst, then heating the reaction mixture until the desired composition, verified by acid value and alkalinity value, is reached. In some embodiments, reduced pressure may be applied during the reaction. The esteramine intermediate is then quaternized using an alkylating agent, yielding an esterquat product.

The fatty acid source for preparing the esterquats can be a variety of starting materials, such as free fatty acids, fatty acid esters, or acid chlorides corresponding to fatty acids. The free fatty acids can be separate, such as a single purified fatty acid, or in combinations, such as fatty acid mixtures characteristic of the fatty acid constituents of glyceride esters in natural oils. In one embodiment, the fatty acid source comprises conjugated linoleic acid (CLA). Fatty acid esters can be glycerides, such as mono-, di- and/or triglycerides, or alkyl esters of fatty acids, such as methyl esters or ethyl esters of fatty acids. The fatty acid esters can be derived from a single fatty acid, or mixtures of fatty acids, such as those derived from natural fatty acid feedstocks or from natural oils.

In some embodiments, the esterquats are prepared by the direct esterification of alkanolamines with the triglycerides in natural oils. When triglycerides are the source of the fatty acids, the resulting esteramine intermediate comprises a mixture of products that include diesteramines, monoesteramines, triglycerides, diglycerides, monoglycerides, glycerin, and free amine. Triglycerides may be obtained from various sources such as, but not limited to, sunflower oil, canola oil, soybean oil, palm oil, palm kernel oil, borage oil, pracaxi oil, walnut oil, jojoba oil, avocado oil, hempseed oil, rapeseed oil, safflower oil, corn oil, cottonseed oil, flaxseed oil, grapeseed oil, peanut oil, cannabis oil, meadowfoam oil, and mixtures thereof. In some embodiments, it is desirable to use an oil having a large amount of unsaturation. Examples of such oils include, but are not limited to, sunflower oil, high oleic acid sunflower oil, canola oil, soybean oil, walnut oil, jojoba oil, borage oil, palm oil, and rapeseed oil, safflower oil, corn oil, cottonseed oil, flaxseed oil, peanut oil, meadowfoam oil, or mixtures thereof. Some preferred natural oils are those that comprise at least 50% by weight of unsaturated fatty acid groups, alternatively at least 60% by weight unsaturated fatty acid groups, having at least one carbon-carbon double bond. In some embodiments, at least 30% by weight, alternatively at least 40% by weight, alternatively at least 50% by weight of the fatty acid groups having at least one carbon-carbon double bond have at least two carbon-carbon double bonds. Preferred natural oils for use herein have a saponification value of less than about 225 and an Iodine Value of 50 or greater, alternatively an Iodine Value of 80 or greater. Examples of suitable unsaturated oils include sunflower oil, comprising about 15% to about 75% by weight, typically about 60% by weight linoleic acid, borage oil, comprising about 35% to about 40% by weight linoleic acid, and safflower oil, comprising about 70% to about 75% by weight linoleic acid.

In other embodiments, the esterquats may be prepared from C8-32 fatty acids, or alkyl ester derivatives thereof, that are saturated, unsaturated or a mixture of saturated and unsaturated fatty acids. The fatty acids may be derived from various sources such as, for example, sunflower, canola, corn, cottonseed, flaxseed, peanut, meadowfoam, soybean, walnut, jojoba, palm, borage, safflower, or rapeseed, or mixtures thereof. Preferred fatty acids comprise at least 50% by weight, alternatively at least 60% by weight unsaturated fatty acid groups having at least one carbon-carbon double bond. In some embodiments, at least 30% by weight, alternatively at least 40% by weight, alternatively at least 50% by weight of the fatty acid groups having at least one carbon-carbon double bond have at least two carbon-carbon double bonds. Preferred fatty acids are also those having carbon chain lengths of 16 to 20 carbon atoms and/or a saponification value of less than 225 and an Iodine Value of 50 or greater, alternatively an Iodine Value of 80 or greater. In one embodiment, the fatty acid comprises CLA, having about 75% to about 90% by weight conjugated linoleic acid (C18-2) groups.

The alkanolamines useful for preparing the esterquats of the present technology correspond to the following general formula:

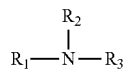

where $R_1$, $R_2$, and $R_3$ are independently selected from $C_{1-6}$ alkyl or hydroxy alkyl groups. Examples of alkanolamines include triethanol amine (TEA), methyl diethanolamine (MDEA), ethyl diethanolamine, dimethyl amino-N-(2,3-propanediol), diethylamino-N-(2,3-propanediol), methylamino-N,—N,-bis(2,3-propanediol), ethylamino-N,N-bis(2,3-propanediol), and mixtures thereof. In some embodiments, the alkanloamine comprises MDEA. In other embodiments, the alkanolamine comprises TEA. The molar ratio of triglyceride/fatty acid to alkanolamine is about 1.4 to about 3, alternatively about 1.5 to 3, alternatively about 1.4 to about 2 moles of acyl groups to 1 mole of amine.

Alkylating agents for preparing the esterquats are known in the art and include, for example, dimethyl sulfate, methyl chloride, diethyl sulfate, benzyl chloride, ethyl benzyl chloride, methyl bromide, and epichlorohydrin. In some embodiments, the alkylating agent comprises methyl chloride in order to prepare an esterquat that is sulfate-free. Hair conditioning compositions and other personal care compositions that are formulated from components that are sulfate-free are more desirable because they are milder and gentler on skin and hair than sulfate-containing compositions.

In addition to the esterquats, compositions of the present technology comprise monoglycerides, diglycerides, or mixtures thereof. In some embodiments, the mono- and diglycerides are byproducts of the reaction between the alkanolamine and the natural oil triglycerides. In such embodiments, the fatty acid carboxylate groups in the mono- and diglycerides are derived from the natural oil source. It should be appreciated that small amounts of triglycerides, glycerol, and free amine may also be present. In other embodiments, the mono- and diglycerides are added as a separate component to the esterquats, and can have carbon chain lengths that are different from the fatty acid chain lengths in the esterquats. Regardless of the source, the mono- and diglycerides comprise saturated, unsaturated, or a mixture of unsaturated and saturated fatty acid carboxylate groups containing about 8 to about 32 carbon atoms. Preferably the fatty acid groups comprise at least 50% by weight, alternatively at least 60% by weight unsaturated fatty acid groups having at least one carbon-carbon double bond. In some embodiments, the fatty acid groups are derived from oleic acid. Typically, the ratio of mono- to diglyceride will be about 1:1, although other ratios are also contemplated, such as 1:3 to 3:1 monoglyceride to diglyceride. In some embodiments, the glyceride component can be 100% monoglycerides. The esterquat comprises about 50% to 80%, alternatively about 55% to about 75%, and the mono- and diglycerides comprise about 20% to about 50%, alternatively about 25% to about 45%, by weight, based on the combined weight of the mixture of esterquat and glycerides.

The mixture of esterquat and mono- and diglycerides can be used alone as an active component, or diluted in particular solvents to form a diluted esterquat composition. In some embodiments, the solvents are those suitable for personal care. Examples of solvents for diluting the esterquat and mono- and diglyceride mixture include, but are not limited to, propylene glycol, 1,3-propandiol, glyceryl esters, glycerol monooleate, glycol ethers, glycerin, sorbitan esters, lactic acid, sunflower oil, jojoba oil, alkyl lactyl lactates, isopropyl alcohol, ethyl alcohol, dimethyl adipate, oleyl alcohol, borage oil, moringa oil, argan oil, 1,2-isopropylidine glycerol, benzyl alcohol, dimethyl lauramide myristamide, N-butyl lactate, trimethyl citrate, dimethyl lactide, laureth-2 lactide, 1,2-butylene carbonate, conjugated linoleic acid, raddish seed oil, isosorbide dimethyl ether, propylene carbonate, sunflower Oil/MDEA esteramine, C-65 esters, citrate, C12-15 alkyl benzoate, or combinations thereof.

When used, the amount of solvent can range from about 1% to about 70%, alternatively about 5% to about 70%, alternatively about 10% to about 60%, alternatively about 10% to about 50%, alternatively about 10% to about 40%, alternatively about 10% to about 30% by weight, and the amount of the mixture of esterquats and mono- and diglycerides can range from about 30% to about 99%, alternatively about 30% to about 95%, alternatively about 30% to about 90%, alternatively about 40% to about 90%, alternatively 50% to about 90%, alternatively about 60% to about 90%, alternatively about 70% to about 90% by weight, based on the weight of the composition. In some embodiments, the amount of solvent is about 10% to about 30% by weight, and the amount of the mixture of esterquats and mono- and diglycerides is about 70% to about 90% by weight, in order to form a high solids esterquat composition. It has been surprisingly discovered that a high solids, low viscosity, pale-colored liquid esterquat composition can be obtained from a mixture of sunflower oil-based esterquat and mono- and diglycerides in an amount of about 85% by weight esterquat/glycerides and about 15% by weight propylene glycol solvent, based on the combined weight of the esterquat/glyceride mixture and solvent. In another embodiment, a high solids, low viscosity, liquid esterquat composition can be obtained from a mixture of sunflower oil-based esterquat and mono- and diglycerides in an amount of about 80% by weight esterquat/glycerides, and about 20% by weight of a solvent comprising the combination of alkyl lactyl lactate and glycerin, based on the combined weight of the esterquat/glyceride mixture and solvent. Such results are surprising because hair conditioning quats, such as BTAC and CETAC, typically are available in liquid form only at dilutions of about 20% to about 30% solids unless flammable solvents are also included.

In some embodiments, the esteramine/glyceride intermediate can be diluted in the solvent prior to quaternization of the immediate. When added during the esterquat manufacturing process, the desired solvent is combined with the esteramine/glyceride intermediate and the alkylating agent, and the quaternization process takes place in the presence of the solvent. The amount of the solvent added can be an amount within any of the ranges recited above. The resulting esterquat composition comprises about 30% to about 99%, alternatively about 30% to about 95%, alternatively about 30% to about 90%, alternatively about 40% to about 90%, alternatively about 50% to about 90%, alternatively about 60% to about 90%, alternatively about 70% to about 90% by weight of the esterquat/glycerides mixture, and about 1% to about 70%, alternatively about 5% to about 70%, alternatively about 10% to about 70%, alternatively about 10% to about 60%, alternatively about 10% to about 50%, alternatively about 10% to about 40%, alternatively about 10% to about 30% by weight of the solvent.

In some embodiments, the composition comprising the mixture of esterquats and mono- and diglycerides can be in the form of a dilutable concentrate or in flaked form, rather than a liquid composition. In a flaked product form, the mixture of esterquats and mono- and diglycerides is typically combined with a long chain fatty alcohol, such as cetearyl alcohol, cetyl alcohol, stearyl alcohol, or combinations thereof, and/or a solvent, such as isopropyl alcohol, ethanol, or esters. The mixture of esterquats and mono- and diglycerides comprises about 10% to about 90% by weight, alternatively about 20% to about 35% by weight, the long chain alcohol comprises 0% to about 90% by weight, alternatively about 55% to about 70% and the solvent comprises about 10% to about 20% by weight, based on the total weight of the flaked product. When long chain alcohols are not present, the flaked product can comprise 80% to 90% by weight of the mixture of esterquats and mono- and diglycerides, and 10% to 20% by weight of solvent, for a high cationic load product. The dilutable concentrate comprises the mixture of esterquats and mono- and diglycerides combined with at least one long chain fatty alcohol such as cetearyl alcohol, cetyl alcohol, stearyl alcohol, or combinations thereof, optionally one or more additional components, and solvent, water, or a combination thereof. Typical solvents for the dilutable concentrate include, but are not limited to, isopropyl alcohol, ethanol, or esters. Additional components can include additives, such as pH adjusters or preservatives. The mixture of esterquats and mono- and diglycerides can comprise about 2% to about 30% by weight of the dilutable concentrate, the long chain fatty alcohol can comprise about 5% to about 25% by weight of the dilutable concentrate, the solvent can comprise about 2% to about 30%, and water can comprise about 25% to about 90% by weight of the dilutable concentrate.

The composition comprising the mixture of esterquats and mono- and diglycerides has a variety of uses, and can be formulated into a variety of end use products. For example, the composition comprising the mixture of esterquat and mono- and diglycerides can be used as a skin feel additive, a cationic emulsifier for skin care, a sun care additive, a textile treatment agent, or a leather conditioner. Examples of end use product formulations in which the mixture of esterquats and mono- and diglycerides can advantageously be used include, but are not limited to, hair conditioners, hair repair compositions, conditioning personal care cleansing products, fabric softeners, fabric conditioners, hard surface cleaners, and skin care compositions. Product formulations can include the mixture of esterquats and glycerides in an amount of about 0.01% to about 30% by weight of the product formulation, alternatively about 0.01% to about 20%, alternatively about 0.01% to about 10%, alternatively about 0.05% to about 7%, alternatively about 0.1% to about 5%, alternatively about 0.5% to about 5%, alternatively about 1% to about 5%, alternatively about 1.5% to about 5%, alternatively about 1.5% to about 4%, alternatively about 2% to about 4% by weight of the product formulation.

The product formulations may contain other optional ingredients suitable for use, such as surfactants or other additives, and a diluent, such as water. Examples of surfactants include nonionic, cationic, and amphoteric surfactants, or combinations thereof. Examples of nonionic surfactants include, but are not limited to, fatty alcohol alkoxylates, polyalkylene glycols, amine oxides, or combinations thereof. Examples of cationics include, but are not limited to, BTAC, CETAC, and polyquaterniums, or combinations thereof. Examples of amphoteric surfactants include, but are not limited to, betaines, amidopropylbetaines, sultaines, amidopropyl hydroxysultaines, or combinations thereof. Other contemplated components include the long chain amido amines, such as stearamidopropyl dimethylamine (SAPDMA). Surfactant amounts in the product formulation can range from about 0.01% to about 25% by weight of the product formulation.

Examples of additives include rheological modifiers, emollients, skin conditioning agents, emulsifier/suspending agents, fragrances, colors, herbal extracts, vitamins, builders, enzymes, pH adjusters, preservatives, and antibacterial agents. Particular examples of such additives include, but are not limited to, silicones, siloxanes, natural oils, mineral oils, natural or synthetic waxes, polyglycerol alkyl esters, glyceryl esters, glycol esters, esters of fatty acids with alcohols of low carbon number, for example isopropanol, benzoic acid esters, vitamins, such as Vitamin A, Vitamin E, or pantothenic acid, quaternized guar, cellulose or quaternized cellulose, or combinations of any of the foregoing. Total additives in the product formulation can range from about 0.01% to about 10% by weight of the product formulation.

Compositions of the present technology, comprising the mixture of esterquats and mono- and diglycerides, provide several benefits. The compositions provide better wet and dry hair combing properties compared to compositions comprising CETAC, and comparable wet and dry combing properties compared to compositions comprising BTAC. However, unlike BTAC and CETAC, the esterquats of the present technology provide less skin irritation, and provide an improved environmental profile and lower aquatic toxicity compared to BTAC and CETAC. Surprisingly, the compositions of the present technology provide improved wet and dry combing properties without the need for additional components, such as fatty acid ethoxylates and alkyl and/or alkenyl oligoglucosides. In some embodiments, the compositions of the present technology, when diluted with an appropriate solvent, provide a high solids, low viscosity liquid composition that is easily formulated with other ingredients to form a final product composition.

Hair conditioning compositions comprising the esterquat/glycerides and solvent of the present technology can be applied to the hair in an amount suitable for obtaining a hair conditioning effect. Suitable amounts of the conditioning active applied to the hair can range from about 0.001% to about 5% by weight, alternatively about 0.001% to about 2%, alternatively about 0.002% to about 1.5%, alternatively about 0.025% to about 0.5%, alternatively about 0.025% to about 0.25% by weight, as measured on dry hair. The hair conditioning compositions, when measured on a Dia-Stron MT1775 instrument, provide a wet combing Maximum Peak Load of about 50 gram mass force (gmf) or less, alternatively about 23 gmf or less, alternatively about 20 gmf or less, alternatively about 8 to about 20 gmf, alternatively about 8 to about 15 gmf.

EXAMPLES

The presently described technology and its advantages will be better understood by reference to the following examples. These examples are provided to describe specific embodiments of the present technology. By providing these examples, the inventors do not limit the scope and spirit of the present technology.

The following test methods are used to determine properties and performance of compositions of the present technology.

Dia-Stron Procedure for Wet and Dry Combing
1. Rinse tress for 30 s.
2. Apply 0.5 mL of VO5® Volumizing Shampoo (non-conditioning shampoo).
3. Spread throughout tress.
4. Rinse tress for 30 s.
5. Allow tress to air-dry.
6. Rinse tress for 30 s.
7. Apply 0.5 mL of Test Conditioner.
8. Spread throughout tress.
9. Rinse tress for 30 s.
10. Affix tress to Dia-Stron MTT175 instrument and run "Wet Combing" procedure.
11. Repeat Step 8 nine more times.
12. Repeat Step 1-10 for 2 more tresses.
13. Allow tresses to air-dry.
14. Affix tress to Dia-Stron MTT175 instrument and run "Dry Combing" procedure.
15. Repeat Step 12 nine more times for one tress.
16. Repeat Steps 12-13 for 2 more tresses.

Example 1A: Preparation of Esterquat Using Natural Oil

Esteramine Intermediate

Sunflower oil in the desired amount was charged to a 3-liter, 4-necked glass reactor equipped with mechanical stirring, a reflux condenser, a thermocouple, and nitrogen blanketing. MDEA was added to the reactor in an amount to obtain a molar ratio of 2 fatty acid groups to 1 amine, and potassium carbonate was added to the reaction mixture. The reaction mixture was stirred at 300 rpm and heated to 160° C. under nitrogen until the free amine content stabilized between 2 and 3%. The resulting ester amine mixture was then cooled to room temperature. It should be appreciated that the resulting esteramine mixture comprises about 70% by weight esteramine, and about 30% by weight glycerides, primarily mono- and diglycerides, as by-products from the reaction of MDEA and the sunflower oil.

Quaternization

The esteramine mixture was then added to a 1-liter pressure reactor equipped with mechanical stirring and heating. The temperature was increased to 105° C. The reactor was pressurized to 20 psig and vented to 0 psig three times with methyl chloride. Methyl chloride was added subsurface to maintain a reactor pressure of 40 psig. Reaction conditions were maintained for 9 hours, and the reactor was cooled to 85° C. and vented to 0 psig. The resulting esterquat mixture had a free amine content of 0.05 meq/g, total acidity of 0.01 meq/g, and cationic actives of 0.95 meq/g. Solids content was 100%.

Dilution

Embodiment 1: The esterquat mixture was diluted by 15% with naturally derived propylene glycol. The diluted product was a low viscosity, pale colored liquid comprising 85% by weight esterquat mixture and 15% by weight propylene glycol.

Embodiment 2: The esterquat mixture was diluted by 20% with a solvent mixture of 15% by weight lauryl lactylactate and 5% by weight glycerin. The diluted product was a low viscosity liquid comprising 80% by weight esterquat mixture and 20% by weight lauryl lactyllactate/glycerin solvent.

Example 1B: Preparation of Esterquat Using Fatty Acid

Esteramine Intermediate

Fatty acid in the desired amount was charged to a suitable sized reactor equipped with a mechanical stirrer, a thermocouple, and a simple distillation apparatus vented to a mineral oil-filled bubbler. A nitrogen sparging tube was attached to the remaining neck of the reactor, and the fatty acid was then sparged with nitrogen while stirring for no less than 1 hour. MDEA was added to the reactor in an amount to obtain a molar ratio of 1.7 moles of fatty acid per mole of amine. The reaction was slowly heated to 160° C. and held at this temperature until the acid value reached 0.06 meq/g or less. The resulting esteramine was then cooled to room temperature. It should be appreciated that when made with fatty acids rather than triglycerides in a natural oil, the resulting esteramine does not contain glycerides.

Quaternization

The fatty acid-derived esteramine intermediate is quaternized in a manner similar to that used for quaternization of the natural oil intermediate.

Example 1C: Preparation of Esterquat Using CLA

Esteramine Intermediate

CLA (CLARINOL® A-80, Stepan Company) in the desired amount was charged to a suitable sized reactor equipped with a thermocouple, a mechanical stirrer, a sparging tube attached to a nitrogen source, and a short path distillation apparatus vented to a mineral oil filled bubbler. The system was placed under a 200 mL/min nitrogen subsurface sparge and allowed to stir overnight at room temperature.

The sparging tube was removed from the liquid but a 200 mL/min headspace purge was maintained. The reaction mixture was heated to 80° C. and MDEA was added to the reactor in an amount to obtain a molar ratio of 1.7 moles of fatty acid per mole of amine. The reaction temperature exothermed, reaching 90.8° C. before beginning to cool. Once the exotherm had completed, the reaction temperature was adjusted to 125° C., the nitrogen purge was adjusted to 300 mL/min, and the reaction was allowed to stir for 1 hour. The temperature was then increased to 155° C. and stirred for 1 hour. The reaction temperature was increased to 190° C., the sparging tube was inserted into the stirring reaction mixture, and the reaction was stirred at 250 rpm while under a 300 mL/min nitrogen subsurface sparge for 5.75 hours until the acid value of the reaction mixture had reached 0.0515 meq/g.

Quaternization

The CLA-derived esteramine intermediate is quaternized in a manner similar to that used for quaternization of the natural oil intermediate.

Esterquats were also prepared from sunflower oil, sunflower fatty acids, palm oil, palm fatty acids, rapeseed oil, rapeseed fatty acids, safflower oil, and safflower fatty acids using the Example 1A or 1B procedures above, but utilizing a different quating agent and/or a different ratio of fatty acid groups to amine. The prepared esterquats are summarized in Table 1 below. In the Table, "GMO" refers to DREWMULSE® GMO, a glyceryl oleate from Stepan Company, Northfield, Illinois, with a mono-oleate/di-oleate ratio of about 1:1.

General Procedure

1. Charge Water, Natrosol 250 HHR CS and mix until homogenous.
2. Adjust pH using Sodium Hydroxide for target of pH 8-9. Mix until homogenous.
3. Mix and heat to 70-75° C.
4. Add Cationic Surfactant and Cetyl Alcohol and mix until homogenous.
5. Cool to 45° C.
6. Charge Potassium Chloride and mix until homogenous.
7. Adjust pH using Citric Acid for target of pH 3.5-4.5.
8. Cool to room temperature.
9. Charge Preservative.

TABLE 1

| | | | Ester Quats Compositional Analysis | | | | | | DiaStron Wet Combability |
|---|---|---|---|---|---|---|---|---|---|
| | Derivative | | | | | | | | |
| | Oil or | | | | | Glycerides/Esters/Alcohols | | | Maximum |
| Feedstock | Fatty Acid | MDEA or TEA | Feedstock:MDEA/TEA | Salt | % TG | % DG | % MG | % Glycerin | Peak Load (gmf) |
| Sunflower | Oil | MDEA | 2:1 | MeCl | 3.8 | 20.34 | 12.88 | 1.58 | 12.6 |
| Sunflower | Oil | MDEA | 1.75:1 | MeCl | | | | | 10.9 |
| Sunflower | Oil | MDEA | 1.5:1 | MeCl | | | | | 9.7 |
| Sunflower | Oil | MDEA | 2:1 | DMS | 2.59 | 13.54 | 12.23 | 1.65 | 20.0 |
| Sunflower | Oil | TEA | 2:1 | DMS | 4.18 | 7.64 | 11.15 | 1.92 | 26.2 |
| Sunflower | Fatty Acid | MDEA | 2:1 | MeCl | | | | | 54.0 |
| | | | | | | Add 30% GMO | | | 13.3 |
| Sunflower | Fatty Acid | MDEA | 1.4:1 | MeCl | | | | | 56.0 |
| | | | | | | Add 30% GMO | | | 9.9 |
| Palm | Oil | MDEA | 2:1 | MeCl | 7.95 | 27.29 | 13.04 | 1.09 | 24.7 |
| Palm | Oil | TEA | 2:1 | DMS | ND | 10.54 | 11.76 | 2.41 | 28.2 |
| Palm | Fatty Acid | TEA | 1.78:1 | DMS | | | | | 70.3 |
| | | | | | | Add 30% GMO | | | 10.5 |
| Palm | Fatty Acid | TEA | 3:1 | DMS | | | | | 60.3 |
| | | | | | | Add 30% GMO | | | 25.1 |
| Rapeseed | Oil | TEA | 1:0.67 | DMS | 15.02 | 24.04 | 9.76 | 0.40 | 14.4 |
| Rapeseed | Oil | TEA | 1:1 | DMS | 30.47 | 20.08 | 8.44 | 0.67 | 17.4 |
| Rapeseed | Oil | TEA | 0.67:1 | DMS | 26.93 | 17.19 | 8.31 | 1.06 | 38.7 |
| Rapeseed | Fatty Acid | TEA | 1.7:1 | DMS | | | | | 20.4 |
| | | | | | | | Add 30% | | 13.2 |

*Fatty Acid values come from manufacturers' CoA.

Example 2: Preparation of Hair Conditioning Composition

Esterquats of the present technology and comparative hair conditioning components were formulated into hair conditioning compositions following the general procedure set forth below. Table 2 shows the general formula used to make the hair conditioning compositions.

TABLE 2

| Material Chemical Name | Material Trade Name | % W/W in Formulation |
|---|---|---|
| Deionized Water | N/A | q.s. to 100.0' |
| Hydroxyethylcellulose | Natrosol ™ 250 HHR CS | 0.7 |
| Sodium Hydroxide | N/A | q.s. |
| Cationic Surfactant | Various | Calculated for 2% total solids |
| Cetyl Alcohol | HallStar® CO-1695 CETYL ALCOHOL NF | 2.0 |
| Potassium Chloride, 10% Solution | N/A | 0.5 |
| Citric Acid | N/A | q.s. |
| Preservative | Kathon ™ CG | q.s. |

Example 3: Mechanical Wet and Dry Combing Evaluation

Figure 2:
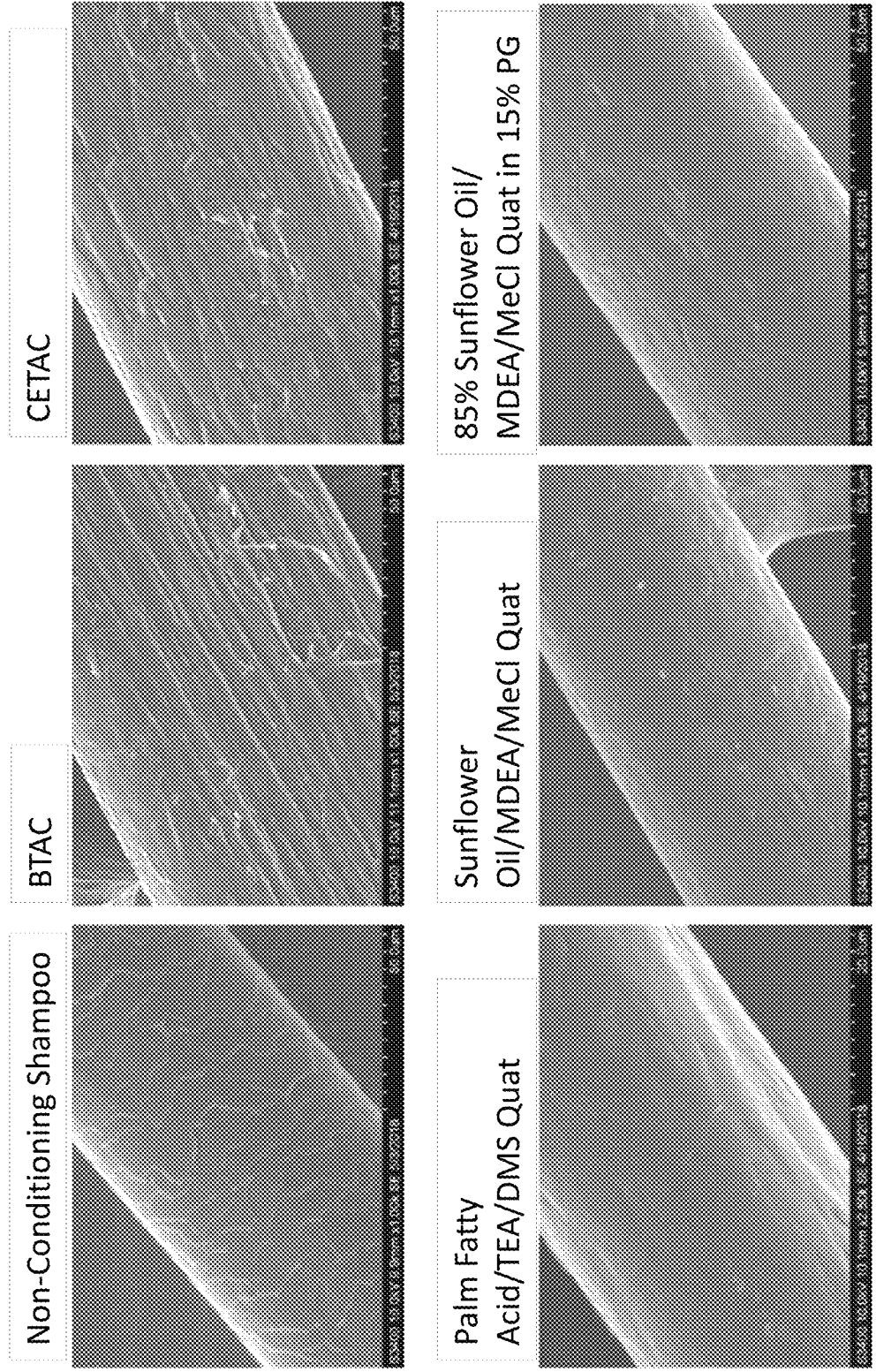
FIG. 2 shows SEM photographs of hair strands treated with hair conditioning compositions of the present technology and with comparative compositions.

The Example 1A sunflower oil-based esterquat composition, undiluted, and the sunflower oil-based esterquat composition diluted in propylene glycol were formulated into hair conditioning compositions in accordance with Example 2. Comparative hair conditioning compositions were also prepared in accordance with the Table 2 formulation and following the General Procedure, except that different cationic surfactants were substituted for the sunflower oil-based esterquat of Example 1A. The comparative cationic surfactants were BTAC, CETAC (AMMONYX®-CETAC-30 from Stepan Company), and STEPANQUAT® GA-90, a palm and TEA-based esterquat from Stepan Company, Northfield, Illinois. The inventive and comparative hair conditioning compositions were tested for wet and dry combing ability using the Dia-Stron MTT175 instrument and the procedure previously described. Also tested were a conventional non-conditioning shampoo, and a blank conditioner formulation prepared in accordance with Table 2 except without the cationic surfactant active. The results of the testing are shown in FIG. 1. SEM photographs of hair strands treated with the inventive and comparative compositions are shown in FIG. 2.

The FIG. 1 graph shows that the compositions prepared with the Example 1A sunflower-oil based esterquats, both undiluted and diluted in propylene glycol, had wet and dry combing comparable to the composition prepared with BTAC, and better performance that the composition prepared with CETAC. The FIG. 1 graph also shows that the sunflower oil-based compositions had better performance than the composition prepared with the palm/TEA esterquat.

Figure 3:
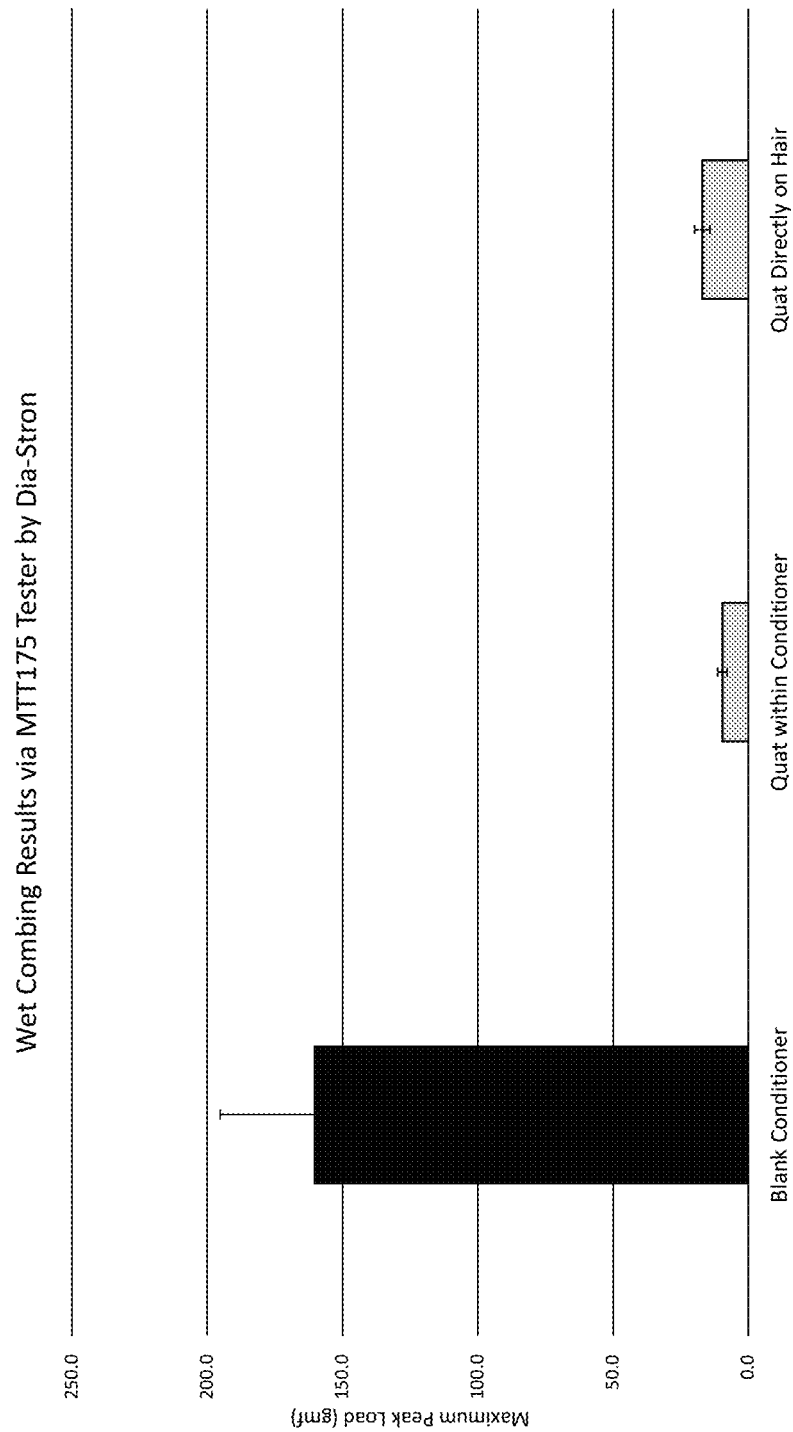
FIG. 3 is a graph comparing the wet combing results of a sunflower oil-based esterquat alone and in a hair conditioning composition.
Figure 4:
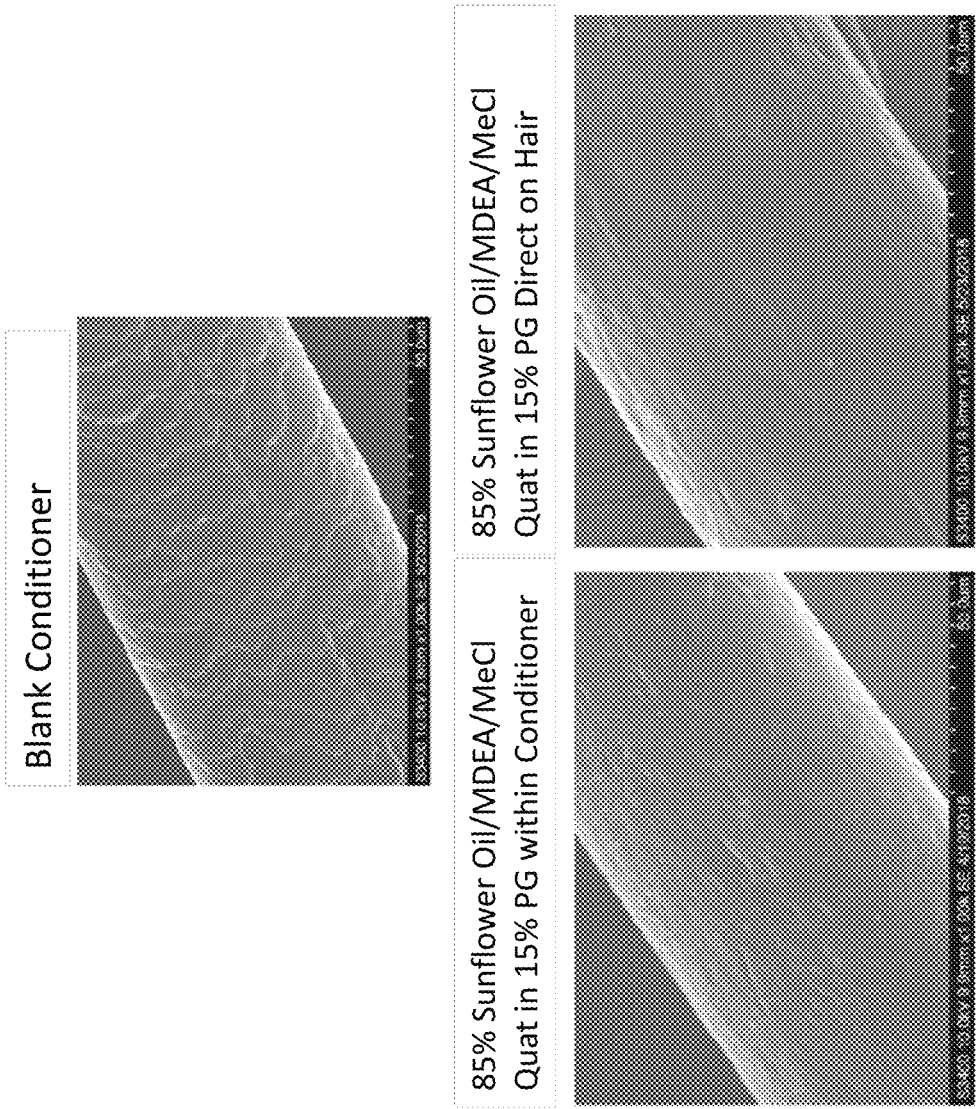
FIG. 4 shows SEM photographs of hair strands treated with (1) a blank hair conditioning composition, (2) a sunflower oil-based esterquat in the hair conditioning composition, and (3) a sunflower oil-based esterquat alone.

Example 4: Wet Combing Evaluation of Hair Conditioner with and without the Sunflower Oil-Based Esterquats A hair conditioning composition was formulated using the Table 2 formulation and using the Example 1A sunflower oil-based esterquat diluted in 15% propylene glycol as the cationic surfactant. The hair conditioning composition was evaluated for wet combing ability using the Dia-Stron MTT175 instrument and the wet combing procedure described above. The hair conditioning composition was also compared with a blank conditioner (the Table 1 formulation without the cationic surfactant), and with the diluted sunflower oil-based esterquat alone (without the conditioner formulation). The results are shown in FIG. 3. SEM photographs of the treated hair stands are shown in FIG. 4.

The graph in FIG. 3 shows that the 85% sunflower oil-based esterquat in propylene glycol provided similar wet combing performance when used alone and in a hair conditioning composition. These results show that the wet combing performance is attributable to the sunflower oil-based esterquat, and does not come from other components in the blank conditioner formulation.

Example 5: Wet Combing Evaluation of Esterquats with and without Glycerides

In this Example, different hair conditioning compositions were prepared to assess whether combining mono- and diglycerides with an esterquat can improve the wet combing properties of the hair care composition compared to compositions containing the esterquat alone. Hair conditioning compositions were formulated using the Table 2 formulation, and using the following as the cationic component in the different compositions:
  Composition 1: 100% mono- and diglycerides
  Composition 2: 100% palm fatty acid esterquat
  Composition 3: 70% palm fatty acid esterquat/30% mono- and diglycerides
  Composition 4: 100% lauryl fatty acid esterquat
  Composition 5: 70% lauryl fatty acid esterquat/30% mono- and diglycerides Each of the hair conditioning compositions was evaluated for wet combing ability using the Dia-Stron MTT175 instrument and the wet combing procedure. The results are shown in FIG. 5.

Figure 5:
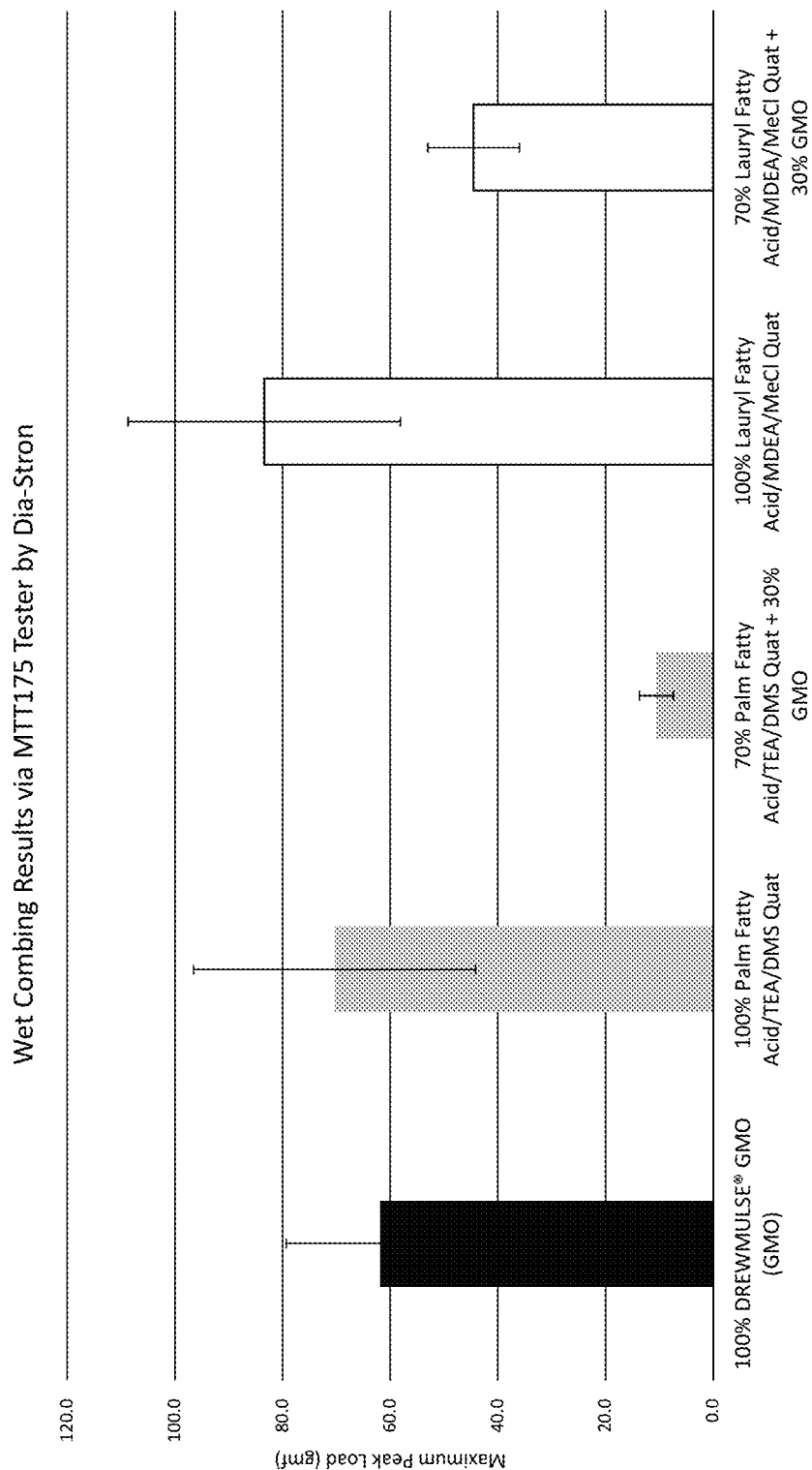
FIG. 5 is a graph comparing the wet combing results of hair conditioning compositions comprising esterquats with and without additional glycerides as the cationic surfactant.

The graph in FIG. 5 shows that the compositions comprising the combination of esterquat and glycerides had better wet combing properties compared to compositions comprising either the esterquat alone or the glycerides alone. The combination of 70% palm fatty acid esterquat and 30% mono- and diglycerides provided an especially notable improvement compared to the composition prepared with 100% palm fatty acid esterquat. The results demonstrate that the combination of esterquats and mono- and diglycerides provides a synergistic mixture that imparts improved properties to a hair conditioning composition when compared to either the esterquat or mono- and diglycerides alone.

Example 6: Wet and Dry Combing Evaluation with Varying Amounts of Glycerides In this example, hair conditioning compositions were prepared to assess the effect of using different ratios of glycerides and esterquats on the wet and dry combing properties of the hair conditioning compositions. Hair conditioning compositions were formulated using the Table 2 formulation, and using the following as the cationic surfactant in the different compositions:
  Composition 1: 100% palm fatty acid esterquat
  Composition 2: 90% palm fatty acid esterquat and 10% glycerides
  Composition 3: 80% palm fatty acid esterquat and 20% glycerides
  Composition 4: 70% palm fatty acid esterquat and 30% glycerides
  Composition 5: 60% palm fatty acid esterquat and 40% glycerides
  Composition 6: 50% palm fatty acid esterquat and 50% glycerides
  Composition 7: 100% sunflower oil esterquat (70% esterquat and 30% glycerides from manufacture)

Each of the hair conditioning compositions was evaluated for wet and dry combing ability using the Dia-Stron MTT175 instrument and the wet and dry combing procedure. The results are shown in FIG. 6.

Figure 6:
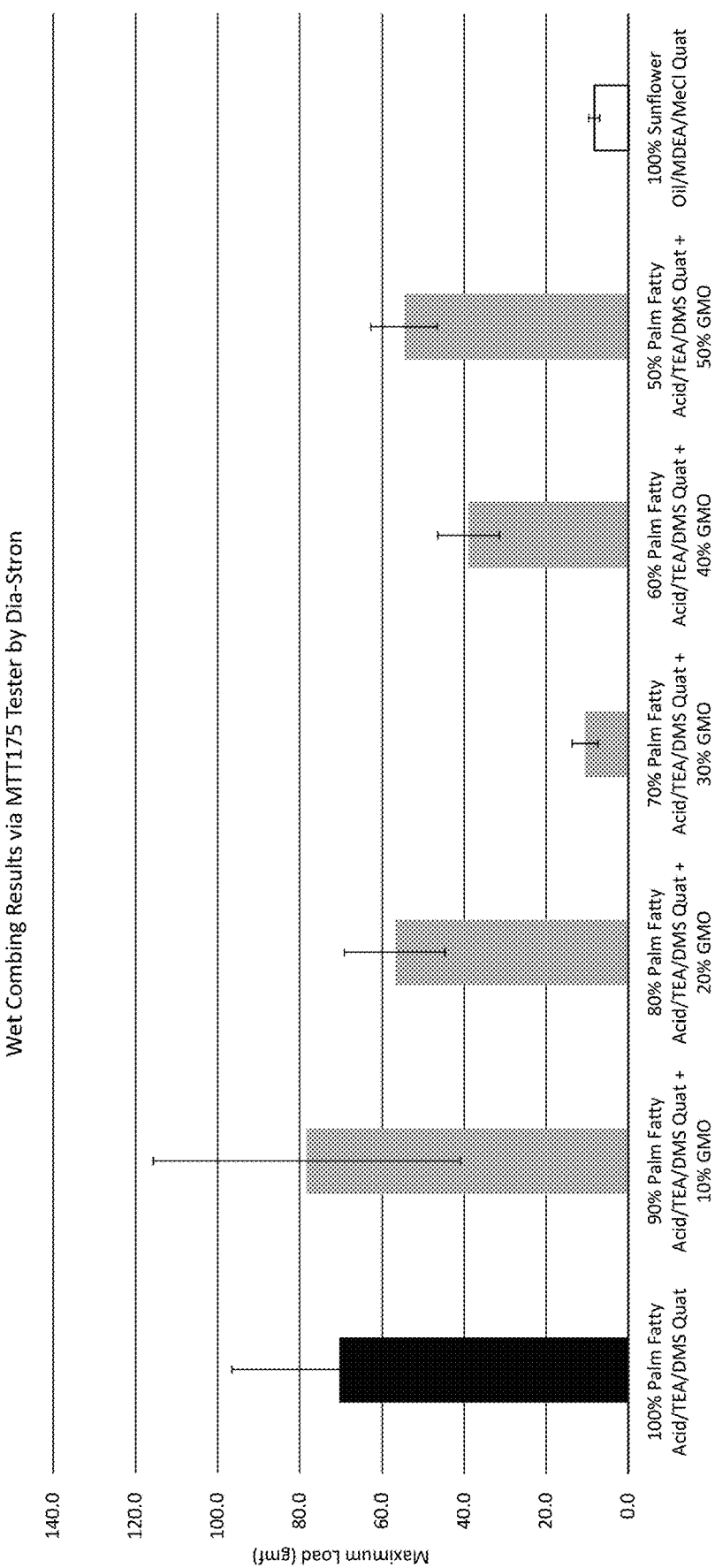
FIG. 6 is a graph comparing the wet combing results of hair conditioning compositions comprising esterquats combined with different amounts of glycerides.

The graph in FIG. 6 shows that significant improvement in performance is achieved with a ratio of 70% esterquat and 30% glycerides compared to esterquat alone and compared to ratios of 90%/10%, 80%/20%, 60%/40% and 50%/50% esterquat and glycerides. Some improvement in performance is also achieved with ratios of 80%/20%, 60%/40%, and 50%/50% esterquat and glycerides when compared to esterquat alone or compared to a ratio of 90%/10% esterquat and glycerides.

Example 7: Wet and Dry Combing Evaluation of Esterquats from Different Oils

In this example, different hair conditioning compositions were formulated to evaluate the effect of using esterquats prepared from different oils on the wet and dry combing properties of the hair conditioning compositions. The different hair conditioning compositions were formulated using the Table 2 formulation, and using the following as the cationic surfactant in the different compositions:
  Composition 1: Sunflower oil esterquat (including glycerides)
  Composition 2: Palm oil esterquat (including glycerides)
  Composition 3: Jojoba oil esterquat (including glycerides)
  Composition 4: Pracaxi oil esterquat (including glycerides)
  Composition 5: Borage oil esterquat (including glycerides)
  Composition 6: Soybean oil esterquat (including glycerides)
  Composition 7: Safflower oil esterquat (including glycerides)

Each of the hair conditioning compositions was evaluated for wet and dry combing ability using the Dia-Stron MTT175 instrument and the wet and dry combing procedure. The results are shown in FIG. 7.

Figure 7:
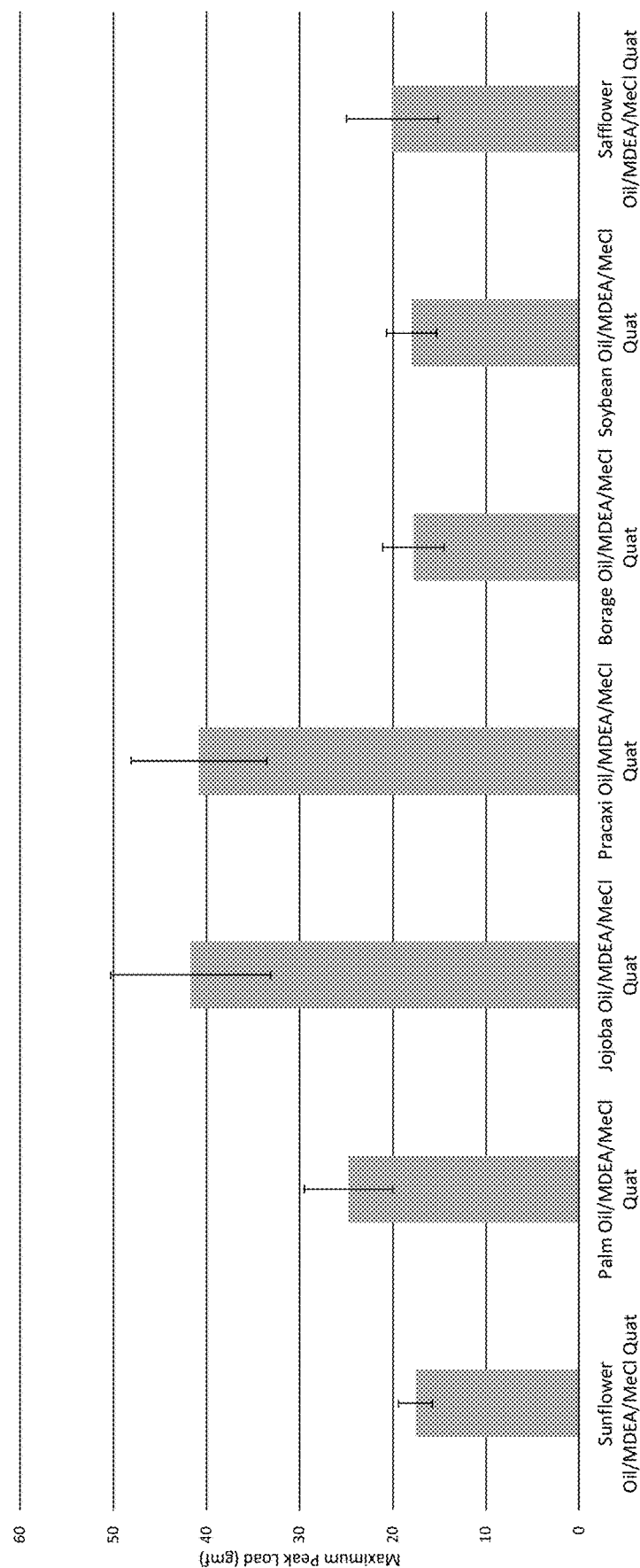
FIG. 7 is a graph comparing the wet combing results of hair conditioning compositions comprising esterquats made from different oils.

The graph in FIG. 7 shows that better results were achieved with the esterquat/glycerides prepared from sunflower oil and borage oil, indicating that carbon chain distribution in the starting oils has an effect on the performance of the resulting esterquat. Sunflower oil and borage oil have appreciable amounts of linoleic acid (60% and 40%, respectively), which may indicate that the amount of polyunsaturation and/or the amount of unsaturated $C_{18}$ in the starting oil has an effect on the performance of the resulting esterquat.

Example 8: Wet Combing Evaluation of Different Glycerides and Different Ratios of Mono- and Diglycerides In this Example, hair conditioning compositions were formulated to evaluate the effect of using unsaturated glycerides and saturated glycerides, and using different ratios of monoglyceride to diglyceride, on the wet combing properties. Hair conditioning compositions were formulated using the Table 2 formulation, and using the following as the cationic component in the different compositions:
Composition 1: 100% palm fatty acid esterquat
Composition 2: 100% DREWMULSE® GMO
Composition 3: 70% palm fatty acid esterquat/30% DREWMULSE® GMO
Composition 4: 100% LUMULSE® GML (a lauric-acid based monoglyceride/diglyceride from Vantage Specialty Chemical)
Composition 5: 70% palm fatty acid esterquat/30% LUMULSE® GML
Composition 6: 100% pure monoglycerides
Composition 7: 70% palm fatty acid esterquat/30% monoglycerides
Composition 8: 50% monoglycerides/50% DREWMULSE® GMO
Composition 9: 70% palm fatty acid esterquat/15% monoglycerides/15% DREWMULSE® GMO Each of the hair conditioning compositions was evaluated for wet combing ability using the Dia-Stron MTT175 instrument and the wet combing procedure. The results are shown in FIG. 8.

Figure 8:
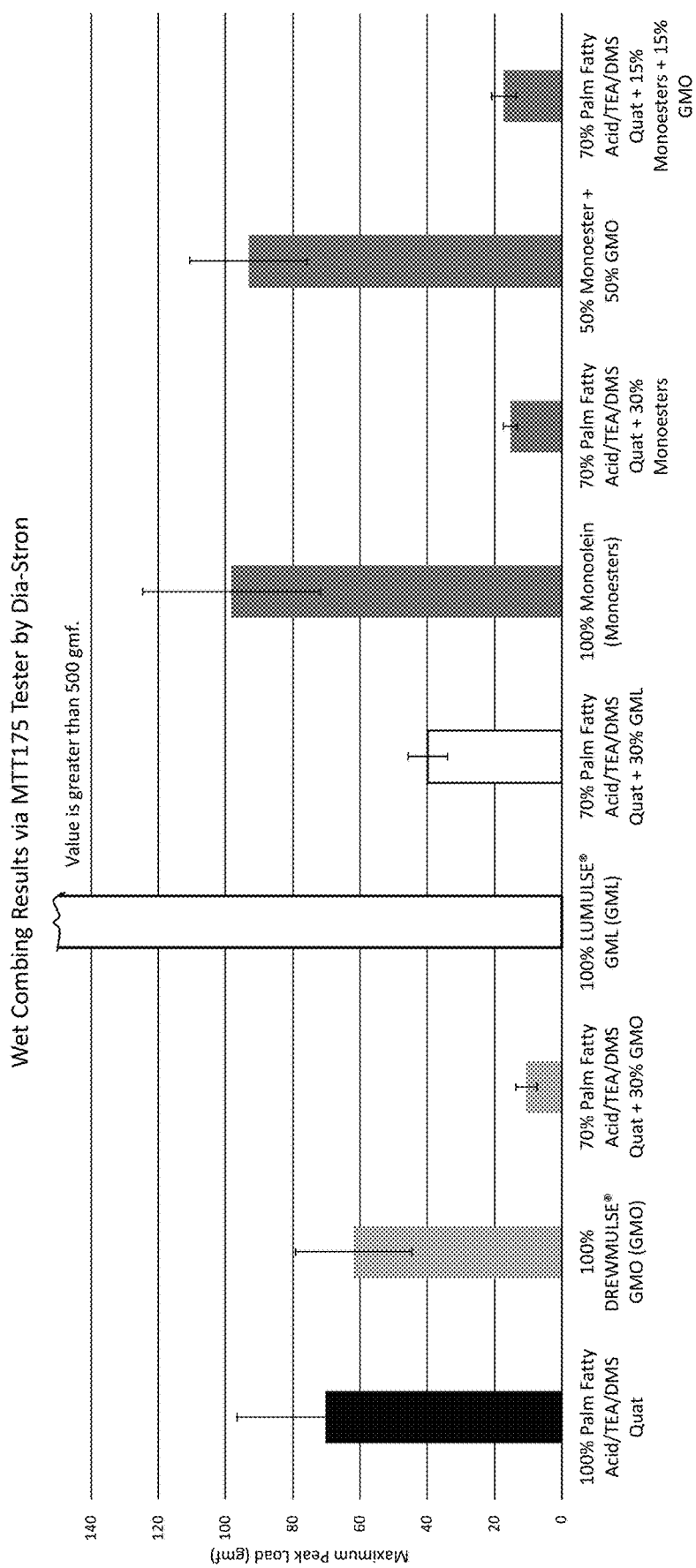
FIG. 8 is a graph comparing the wet combing results of hair conditioning compositions comprising different glycerides and different ratios of mono- and diglycerides.

The graph in FIG. 8 shows that the compositions comprising the 70% esterquat/30% glycerides had better wet combing properties than either the esterquat alone or the glycerides alone. Composition 3, comprising 70% esterquats and 30% DREWMULSE® GMO (unsaturated fatty acid glycerides), provided better wet combing than Composition 5, comprising 70% esterquats and 30% LUMULSE® GML (saturated fatty acid glycerides), indicating that unsaturation in the glyceride component may contribute to improved wet combing performance. There was no significant difference in performance between the compositions comprising different ratios of monoglycerides to diglycerides. Composition 3 comprising a 1:1 ratio of mono- to diglycerides, Composition 7, comprising 100% monoglycerides, and Composition 9, comprising a 3:1 ratio of mono- to diglycerides, showed fairly comparable wet combing properties.

Example 9: Wet Combing Evaluation of the Esterquat/Glyceride Mixture Compared to Esterquats with Other Esters In this example, different hair conditioning compositions were prepared to assess the wet combing properties of a composition of the present technology, prepared with a 70% esterquat/30% glycerides mixture, compared to compositions prepared by replacing the glyceride component with other common conditioning agents. Hair conditioning compositions were formulated using the Table 2 formulation, and using the following as the cationic component in the different compositions:
Composition 1: 100% palm fatty acid esterquat
Composition 2: 70% palm fatty acid esterquat/30% glycerides
Composition 3: 70% palm fatty acid esterquat and 30% glyceryl caprylate/caprate (STEPAN-MILD® GCC)
Composition 4: 70% palm fatty acid esterquat and 30% caprylic/capric triglycerides (NEOBEE® M-5)
Composition 5: 70% palm fatty acid esterquat and 30% isopropyl myristate
Composition 6: 70% palm fatty acid esterquat and 30% glycol distearate
Composition 7: 70% palm fatty acid esterquat and 30% Vitamin E (Tocopheryl acetate)
Composition 8: 70% palm fatty acid esterquat and 30% C12-15 alkyl benzoate Each of the hair conditioning compositions was evaluated for wet combing ability using the Dia-Stron MTT175 instrument and the wet combing procedure. The results are shown in FIG. 9.

Figure 9:
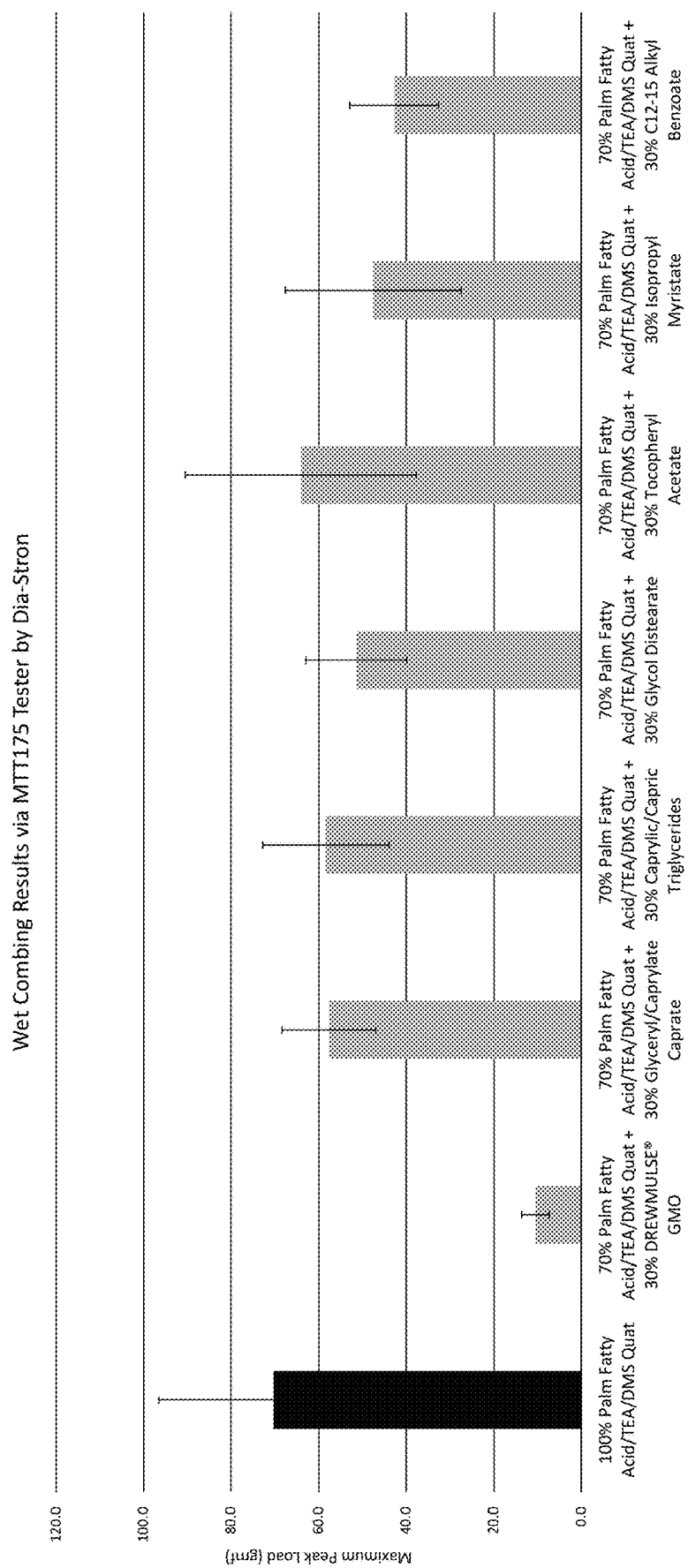
FIG. 9 is a graph comparing the wet combing results of hair conditioning compositions comprising esterquats combined with different esters.

The graph in FIG. 9 shows that the composition comprising the 70% esterquat/30% glycerides had significantly better wet combing properties than any of the compositions comprising esterquats combined with other esters. The results further demonstrate that the combination of esterquats and mono- and diglycerides provides a synergistic mixture that imparts improved properties to a hair conditioning composition when compared to esterquats combined with other esters.

Example 10: Evaluation of Different Oil or Fatty Acid/Amine Ratios

This example evaluates whether changing the ratio of fatty acid groups to amine during esterquat manufacture has an effect on the wet combing properties of compositions formulated with the resulting esterquat. Esterquats were prepared generally following the procedure of Example 1A or 1B, except that the molar ratio of fatty acid groups to amine was varied. The following esterquats were prepared:
Esterquat 1: Sunflower oil/MDEA (2:1 molar ratio)
Esterquat 2: Sunflower oil/MDEA (1.75:1 molar ratio)
Esterquat 3: Sunflower oil/MDEA (1.5:1 molar ratio)
Esterquat 4: Sunflower fatty acid/MDEA (1.4:1 molar ratio)
Esterquat 5: 70% sunflower fatty acid/MDEA (1.4:1 molar ratio) and 30% mono- and diglyceridesglycerides
Esterquat 6: Sunflower fatty acid/MDEA (2:1 molar ratio)
Esterquat 7: 70% sunflower fatty acid/MDEA (2:1 molar ratio) and 30% mono- and diglyceridesglycerides It should be appreciated that Esterquats 1-3 further include 30% by weight glycerides as by-products of the reaction. Esterquats 4 and 6 contain 100% esterquat and no glycerides, and for Esterquats 5 and 7, glycerides were mixed with the esterquats to obtain a 70% esterquat/30% glycerides mixture. Each of the esterquat/glycerides was formulated into a hair conditioning composition in accordance with the Table 2 formulation, using the esterquat/glycerides as the cationic component. The hair conditioning compositions were evaluated for wet combing ability using the Dia-Stron MTT175 instrument and the wet combing procedure. The results are shown in FIG. 10.

Figure 10:
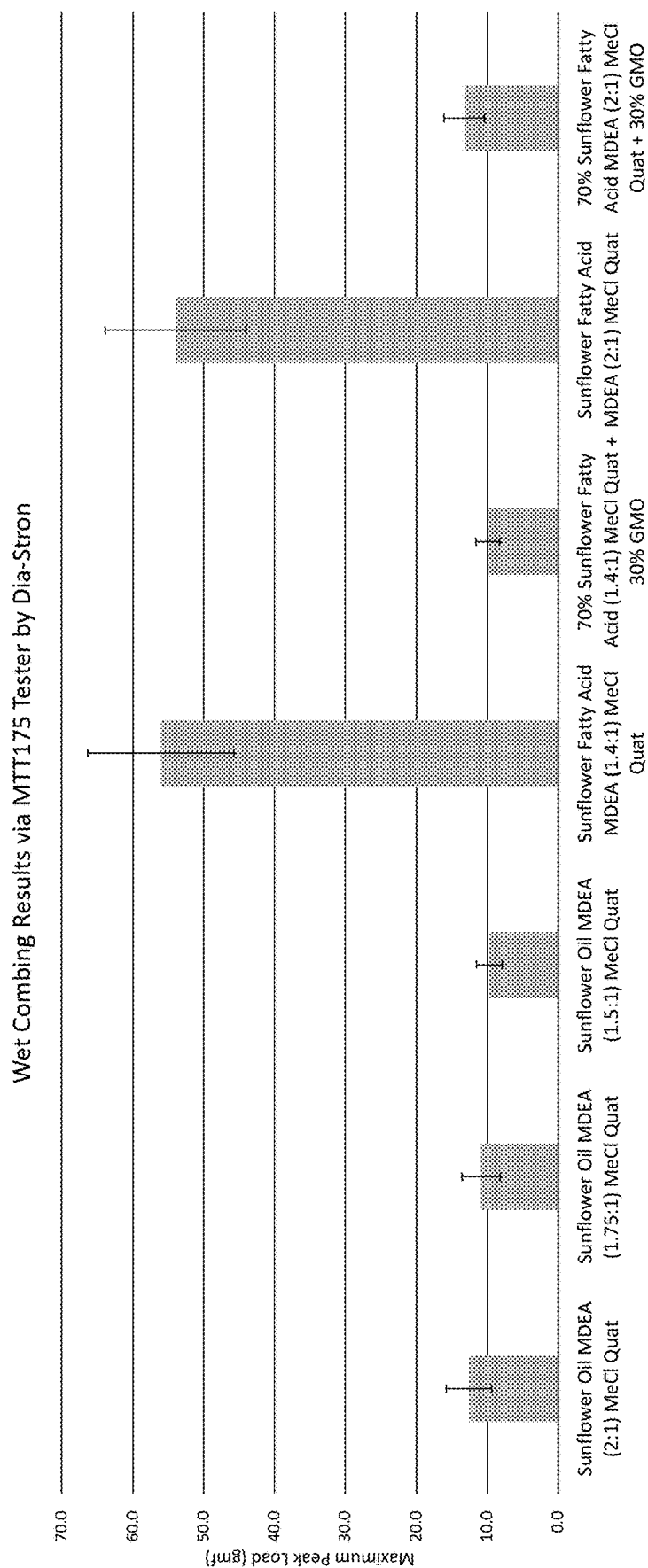
FIG. 10 is a graph comparing the wet combing results of hair conditioning compositions comprising esterquats made with different oil/fatty acid to amine ratios.

The graph in FIG. 10 shows that the fatty acid to amine ratio can be varied from about 1.4 to about 2:1 without significantly changing the wet combing properties of compositions formulated with a mixture of esterquats and glycerides.

Example 11: Wet Combing Evaluation of Added Triglycerides

When natural oil triglycerides are reacted with alkanolamine, small amounts of unreacted triglycerides (up to about 5% by weight) remain in the esterquat/glycerides mixture. In this example, sunflower oil (triglycerides) was added to palm fatty acid-derived esterquats to assess the effect of adding triglycerides, rather than mono- and/or diglycerides, to the esterquats. Hair conditioning compositions were prepared in accordance with the Table 2 formulation, using the following as the cationic component in the different formulations:
 Composition 1: 100% palm fatty acid/TEA esterquat
 Composition 2: 90% palm fatty acid/TEA esterquat and 10% sunflower oil
 Composition 3: 80% palm fatty acid/TEA esterquat and 20% sunflower oil
 Composition 4: 70% palm fatty acid/TEA esterquat and 30% sunflower oil
 Composition 5: 60% palm fatty acid/TEA esterquat and 40% sunflower oil Each of the hair conditioning compositions was evaluated for wet combing ability using the Dia-Stron MTT175 instrument and the wet combing procedure. The results are shown in FIG. 11.

Figure 11:
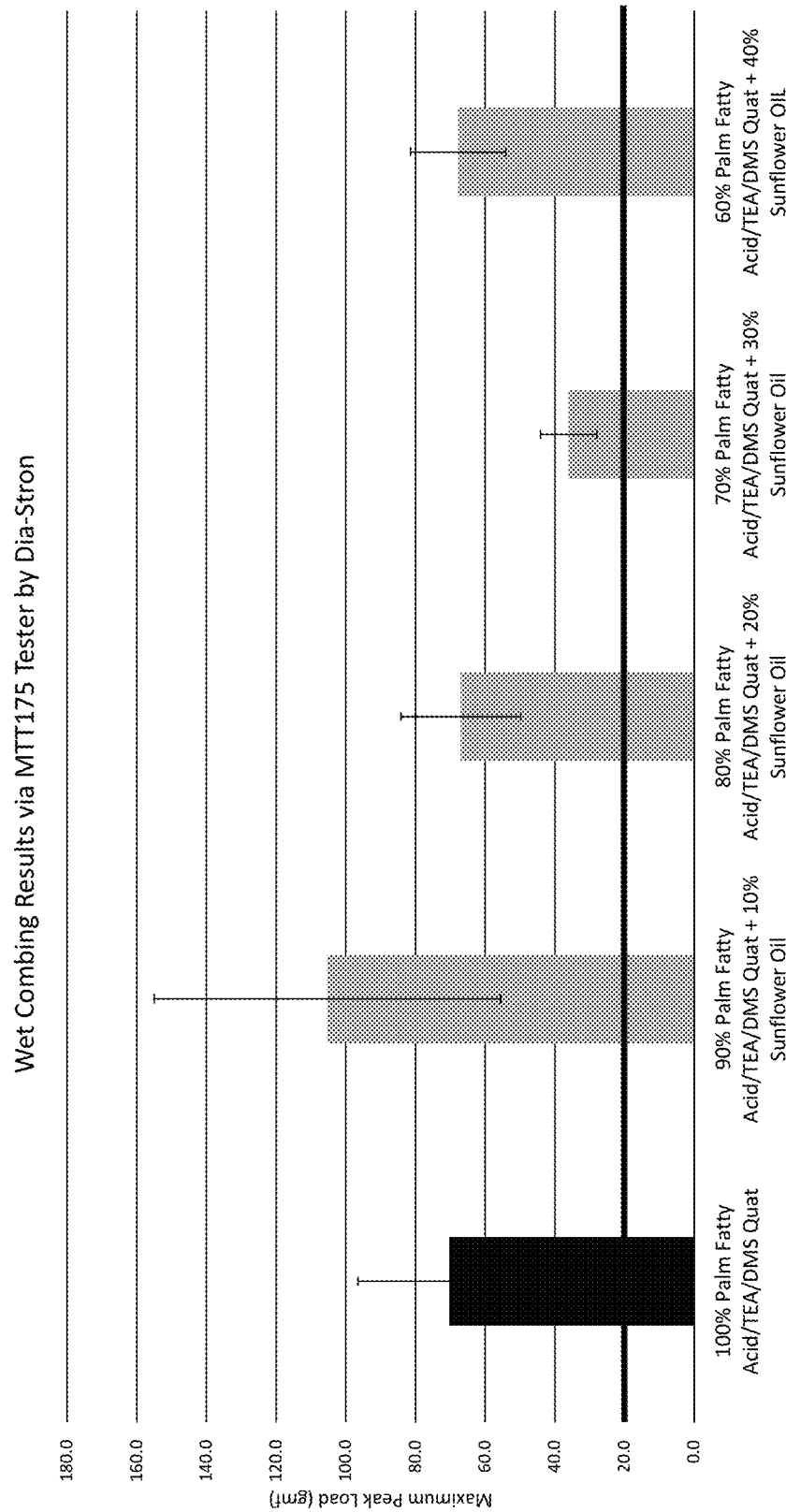
FIG. 11 is a graph comparing the wet combing results of hair conditioning compositions comprising palm fatty acid-derived esterquats combined with different amounts of sunflower oil.

The graph in FIG. 11 shows that adding 30% by weight sunflower oil to the palm fatty acid esterquat can provide some improvement in wet combing properties compared to the palm fatty acid esterquat alone. However, the wet combing properties are still significantly inferior to those obtained from palm fatty acid combined with 30% by weight mono- and diglycerides. See, e.g., Composition 4 in Example 6 and the results shown in FIG. 6 for the 70% esterquat/30% glycerides mixture. FIG. 11 also shows that adding 10%, 20%, or 40% by weight sunflower oil did not improve the performance of the esterquat alone, and 10% added sunflower oil actually provided the worst results.

Example 12: Wet Combing Evaluation of Esterquat/Glycerides Combined with Other Additives Hair conditioning compositions were prepared using the Example 1A, embodiment 2 sunflower oil-based esterquat/glycerides mixture diluted in glycerin/alkyl lactyllactate solvent mixture, either alone or in combination with other additives typically used in hair conditioning compositions. Compositions were prepared utilizing the sunflower oil-based esterquat/glycerides mixture in amounts of 1%, 1.5%, and 2% by weight, based on the total weight of the composition. The compositions prepared with sunflower oil-based esterquat/glycerides in combination with another additive comprised 1% by weight sunflower oil-based esterquat/glycerides and 0.5% by weight other additive, based on the total weight of the composition. The compositions were prepared in accordance with the formulation in Table 2, except adjusting with water to account for the lower amount of the active component. The additives tested were BTAC, CETAC, SAPDMA, sunflower oil MDEA esterammonium lactate, silicone (dimethicone), cationic guar (guar hydroxypropyltrimonium chloride), lauryl lactyl lactate (STEPAN-MILD® L3), and safflower oil. Each of the sample compositions were evaluated for wet combing ability using the Dia-Stron MTT175 instrument and the wet combing test procedure. The results are shown in FIG. 12.

Figure 12:
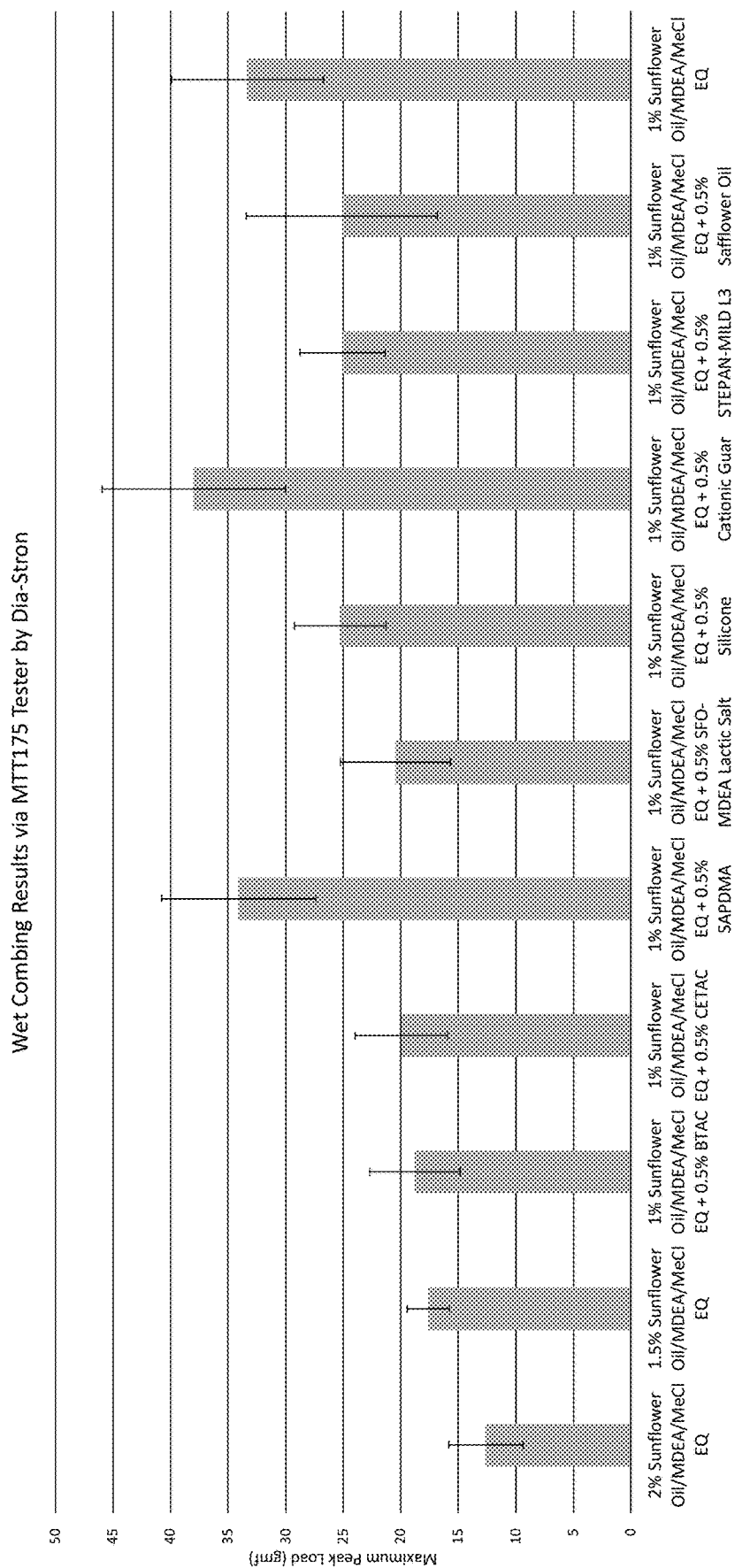
FIG. 12 is a graph comparing the wet combing results of hair conditioning compositions comprising esterquats/glycerides with and without other additives.

The graph in FIG. 12 shows that utilizing 1.5% by weight of the sunflower oil-based esterquat/glycerides mixture alone gave equal or better results than the combinations of 1% by weight sunflower oil-based esterquat/glycerides mixture and 0.5% by weight additive. No improvement in wet combing performance was seen by combining another conditioning additive with the sunflower oil-based esterquat/glycerides mixture compared to the sunflower oil-based esterquat/glycerides mixture alone, at the same 1.5% by weight conditioning active concentration.

Example 13: Wet Combing Evaluation of Esterquats from Different Oils and CLA

In this example, different hair conditioning compositions were formulated to compare the effect of using esterquats prepared from sunflower oil, safflower oil, and CLA on the wet combing properties of the hair conditioning compositions. The different hair conditioning compositions were formulated using the Table 2 formulation, and using the following as the cationic surfactant in the different compositions:
 Composition 1: Sunflower oil esterquat (including glycerides)
 Composition 2: Safflower oil esterquat (including glycerides)
 Composition 3: CLA esterquat, no glycerides Each of the hair conditioning compositions was evaluated for wet combing ability using the Dia-Stron MTT175 instrument and the wet combing procedure. The results are shown in FIG. 13.

Figure 13:
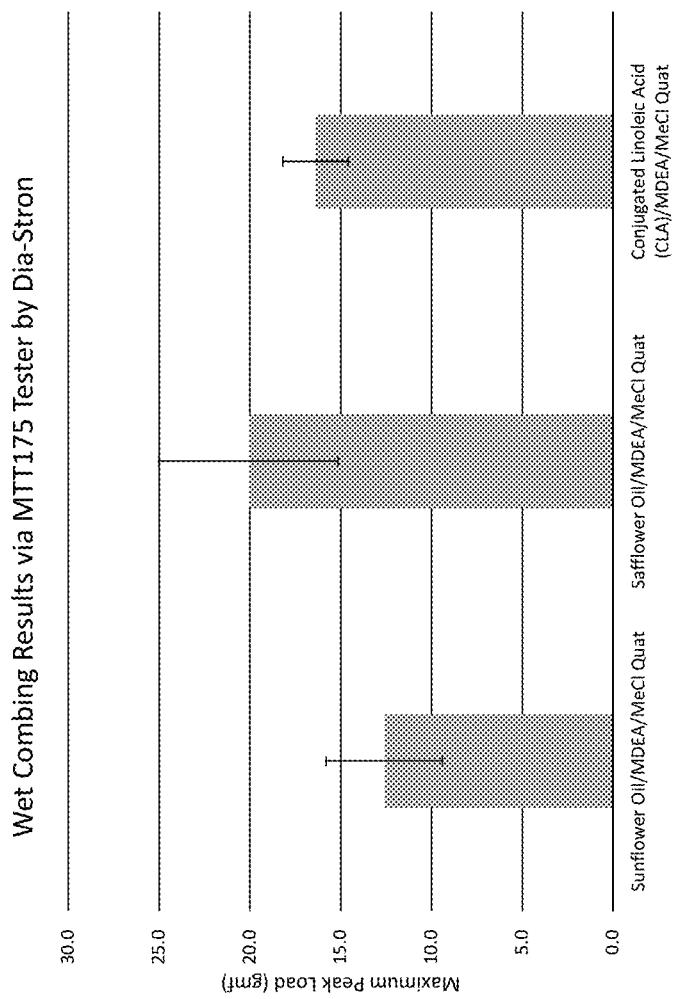
FIG. 13 is a graph comparing the wet combing results of hair conditioning compositions comprising esterquats made from sunflower oil, safflower oil, or conjugated linoleic acid.

The graph in FIG. 13 shows that excellent results were achieved for all of the compositions, indicating that carbon chain distribution and/or the amount of unsaturation in the starting oil or fatty acid may have an effect on the performance of the resulting esterquat. Sunflower oil and safflower oil have appreciable amounts (greater than 80% by weight based on the weight of the oil) of unsaturated C18 fatty acids (oleic acid and linoleic acid). CLA comprises greater than 90% by weight, based on the weight of the CLA, of unsaturated C18 fatty acids, primarily linoleic acid (greater than 70% by weight based on the weight of the CLA). These results show that esterquats prepared from oils or fatty acids having high amounts of C18 unsaturation can provide excellent wet combing properties when formulated into hair conditioning compositions. Surprisingly, the composition prepared with CLA esterquat, without glycerides, performed as well as the compositions prepared with sunflower oil esterquat and safflower oil esterquat, which both included glycerides. This result is surprising because the Dia-Stron data in Table 1, as well as the experimental results from Examples 5 and 6, show that fatty acid esterquats without the addition of about 30% glycerides have Dia-Stron maximum peak loads of greater than 20 gmf.

Example 14: Wet Combing Evaluation of Palm Fatty Acid Esterquats Combined with Different Amounts of CLA Esterquats In this example, different hair conditioning compositions were formulated to evaluate the effect of adding greater polyunsaturation to palm fatty acid esterquats by combining the palm fatty acid esterquats with different amounts of CLA esterquats. The different hair conditioning compositions were formulated using the Table 2 formulation, and using the following as the cationic surfactant in the different compositions:

Composition 1: 100% palm oil fatty acid esterquat
Composition 2: 75% palm oil fatty acid esterquat/25% CLA esterquat
Composition 3: 50% palm oil fatty acid esterquat/50% CLA esterquat
Composition 4: 25% palm oil fatty acid esterquat/75% CLA esterquat
Composition 5: 100% CLA esterquat Each of the hair conditioning compositions was evaluated for wet combing ability using the Dia-Stron MTT175 instrument and the wet combing procedure. The results are shown in FIG. 14.

Figure 14:
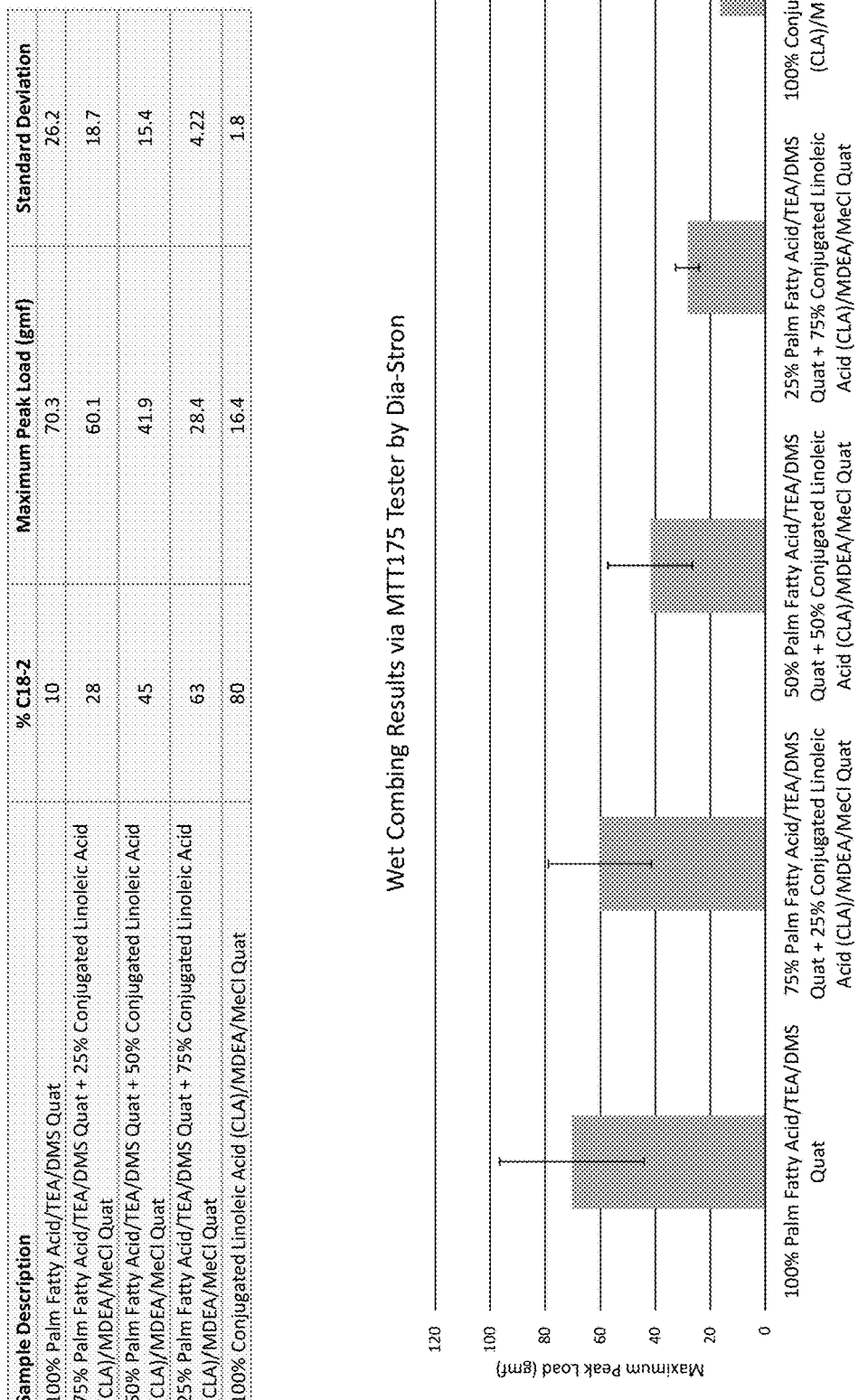
FIG. 14 is a graph comparing the wet combing results of hair conditioning compositions comprising esterquats made from palm fatty acids combined with different amounts of esterquats made from conjugated linoleic acid.

The graph in FIG. 14 shows that better wet combing performance is achieved with increasing amounts of CLA esterquat in the palm fatty acid esterquat/CLA esterquat mixture. The best wet combing properties were achieved with the composition comprising 100% CLA esterquat. About 80% of the fatty acid chains in the CLA esterquat are linoleic acid chains, further demonstrating that the amount of polyunsaturated fatty acid chains in the esterquat may contribute to improved wet combing performance.

The present technology is now described in such full, clear and concise terms as to enable a person skilled in the art to which it pertains, to practice the same. It is to be understood that the foregoing describes preferred embodiments of the present technology and that modifications may be made therein without departing from the spirit or scope of the present technology as set forth in the appended claims. Further, the examples are provided to not be exhaustive but illustrative of several embodiments that fall within the scope of the claims.

The invention claimed is:

1. A composition comprising:
   (A) about 30% to about 100% by weight, based on the weight of the composition, of a mixture comprising:
      (i) one or more esterquats, wherein the esterquats comprise about 55% to about 75% by weight of the mixture, and wherein the esterquats are the quaternized reaction product of (a) a fatty acid source having at least 50% by weight of unsaturated fatty acid groups and carbon chain lengths of 8 to 32 carbon atoms reacted with (b) an alkanolamine, wherein the alkanolamine is triethanolamine (TEA) or methyldiethanolamine (MDEA), in a ratio of 1.5 moles to 3 moles of acyl groups per mole of alkanolamine; and
      (ii) one or more glycerides, wherein the glycerides comprise about 25% to about 45% by weight of the mixture, and wherein the glycerides comprise monoglycerides, diglycerides, or a combination thereof and have at least 50% by weight of unsaturated fatty acid groups; and
   (B) optionally, 0% to about 70% by weight of the composition of a solvent.

2. The composition of claim 1, wherein the fatty acid source is a natural oil.

3. The composition of claim 2, wherein the natural oil is selected from the group consisting of sunflower oil, canola oil, soybean oil, walnut oil, jojoba oil, palm oil, borage oil, rapeseed oil, safflower oil, and mixtures thereof.

4. The composition of claim 2, wherein the natural oil is sunflower oil.

5. The composition of claim 1, wherein the fatty acid source for the esterquats comprises fatty acids derived from one or more fats or oils.

6. The composition of claim 1, wherein the fatty acid source comprises fatty acid alkyl esters.

7. The composition of claim 1, wherein the fatty acid source has a saponification value of less than about 225 and an Iodine Value of greater than 80.

8. The composition of claim 1, wherein at least 60% of the carbon chains in the fatty acid source for the esterquats have at least one carbon-carbon double bond.

9. The composition of claim 8, wherein at least 50% of the carbon chains having at least one carbon-carbon double bond have at least two carbon-carbon double bonds.

10. The composition of claim 1, wherein the monoglycerides, diglycerides, or combination thereof have carbon chain lengths of 8-32 carbon atoms.

11. The composition of claim 10, wherein the glycerides are monoglycerides and diglycerides in a ratio of 3:1 to 1:3.

12. The composition of claim 1, wherein the solvent is selected from the group consisting of propylene glycol, glyceryl caprylate/caprate esters, glycol ethers, glycerin, sunflower oil, jojoba oil, alkyl lactyl lactates, isopropyl alcohol, and combinations thereof.

13. The composition of claim 3, wherein the mixture is the quaternized direct esterification reaction product of sunflower oil reacted with methyl diethanolamine in a ratio of acyl groups to amine of 1.5:1 to 2:1.

14. A formulation comprising:
   (A) 0.01% to about 30% by weight of a composition active comprising:
      (i) one or more esterquats in an amount of about 55% to about 75%, based on the weight of the composition active, wherein the esterquats are the quaternized reaction product of (a) a fatty acid source having at least 50% by weight of unsaturated fatty acid groups and carbon chain lengths of 8 to 32 carbon atoms reacted with (b) an alkanolamine, wherein the alkanolamine is triethanolamine (TEA) or methyldiethanolamine (MDEA) in a ratio of 1.5 moles to 3 moles of acyl groups per mole of alkanolamine; and
      (ii) one or more glycerides in an amount of about 25% to about 45% by weight based on the weight of the composition active, wherein the glycerides comprise monoglycerides, diglycerides, or a combination thereof, and have at least 50% by weight of unsaturated fatty acid groups;
   (B) optionally, one or more additional components; and
   (C) diluent to balance the formulation to 100%.

15. The formulation of claim 14, wherein the formulation is a hair care composition, and wherein the hair care composition, when applied to a hair tress, provides a wet combing Dia-Stron maximum peak load of about 40 gmf or less.

16. The composition of claim 1, wherein the mixture of one or more esterquats and one or more glycerides comprises from 70% to 90% by weight of the composition, and the solvent comprises from 10% to 30% by weight of the composition.

17. The composition of claim 16, wherein the solvent is a mixture of alkyl lactyl lactate and glycerin.

18. The composition of claim 17, wherein the composition is a liquid.

* * * * *